US009497945B2

(12) United States Patent
Kyratsous et al.

(10) Patent No.: US 9,497,945 B2
(45) Date of Patent: Nov. 22, 2016

(54) HUMANIZED DIPEPTIDYL PEPTIDASE IV (DPP4) ANIMALS

(71) Applicant: Regeneron Pharmaceuticals, Inc., Tarrytown, NY (US)

(72) Inventors: Christos Kyratsous, New York, NY (US); Alexander Mujica, Elmsford, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 14/723,855

(22) Filed: May 28, 2015

(65) Prior Publication Data
US 2016/0007579 A1 Jan. 14, 2016

Related U.S. Application Data

(60) Provisional application No. 62/005,476, filed on May 30, 2014, provisional application No. 62/051,626, filed on Sep. 17, 2014, provisional application No. 62/072,692, filed on Oct. 30, 2014.

(51) Int. Cl.
*A01K 67/00* (2006.01)
*A01K 67/027* (2006.01)
*C12Q 1/70* (2006.01)
*C12Q 1/68* (2006.01)
*G01N 33/569* (2006.01)

(52) U.S. Cl.
CPC ............. *A01K 67/0278* (2013.01); *C12Q 1/68* (2013.01); *C12Q 1/6883* (2013.01); *C12Q 1/70* (2013.01); *C12Y 304/14005* (2013.01); *G01N 33/56983* (2013.01); *A01K 2207/15* (2013.01); *A01K 2217/072* (2013.01); *A01K 2227/105* (2013.01); *A01K 2267/01* (2013.01); *A01K 2267/03* (2013.01); *A01K 2267/0337* (2013.01)

(58) Field of Classification Search
None
See application file for complete search history.

(56) References Cited

U.S. PATENT DOCUMENTS

| | | | |
|---|---|---|---|
| 6,586,251 B2 | 7/2003 | Economides et al. | |
| 7,294,754 B2 | 11/2007 | Poueymirou et al. | |
| 7,576,259 B2 | 8/2009 | Poueymirou et al. | |
| 7,659,442 B2 | 2/2010 | Poueymirou et al. | |
| 8,110,720 B2 * | 2/2012 | Ferrara | A01K 67/0275 536/23.1 |
| 8,759,105 B2 | 6/2014 | Economides et al. | |
| 2004/0120924 A1* | 6/2004 | Hone | A61K 31/7024 424/85.1 |
| 2015/0351372 A1 | 12/2015 | Kyratsous et al. | |

FOREIGN PATENT DOCUMENTS

| | | |
|---|---|---|
| WO | WO-02/066630 A1 | 8/2002 |
| WO | WO-2004/104216 A2 | 12/2004 |
| WO | WO-2004/104216 A3 | 12/2004 |
| WO | WO-2006/128163 A2 | 11/2006 |
| WO | WO-2006/128163 A3 | 11/2006 |
| WO | WO-2010/110914 A2 | 9/2010 |
| WO | WO-2010/110914 A3 | 9/2010 |
| WO | WO-2012/071592 A2 | 5/2012 |
| WO | WO-2012/071592 A3 | 5/2012 |
| WO | WO-2013/063556 A1 | 5/2013 |
| WO | WO-2014/045254 A2 | 3/2014 |
| WO | WO-2014/045254 A3 | 3/2014 |
| WO | WO-2015/184164 A1 | 12/2015 |

OTHER PUBLICATIONS

Mullins et al. Journal of Clinical Investigation, 1996.*
Moreadith et al., J. Mol. Med., 1997;75:208-16.*
Pera et al. Journal of Cell Science 2000; 113: 5-10.*
Kuroiwa et al. Nature Genetics 2004;36:775-80.*
Simenoi et al. Hum Immunol 2002;63:719-30.*
Lu et al. Nature 2013;500:227-32.*
Auerbach, W. et al. (Nov. 2000). "Establishment and Chimera Analysis of 129/SvEv- and C57BL/6-Derived Mouse Embryonic Stem Cells," *BioTechniques* 29(5): 1024-1032.
Cockrell, A.S. et al. (May 2014, e-published Feb. 26, 2014). "Mouse Dipeptidyl Peptidase is Not a Functional Receptor for Middle East Respiratory Syndrome Coronavirus (MERS-CoV) Infection," *J. Virol.* 88(9):5195-5199.
Coleman, C.M. et al. (Feb. 2014, e-published Nov. 6, 2013). "Wild-Type and Innate Immune-Deficient Mice are Not Susceptible to the Middle East Respiratory Syndrome Coronavirus," *J. Gen. Virol.* 95(Pt 2):408-412.
Festing, M.F. et al. (Aug. 1999). "Revised Nomenclature for Strain 129 Mice," *Mamm Genome* 10(8):836.

(Continued)

*Primary Examiner* — Janice Li
(74) *Attorney, Agent, or Firm* — Mintz Levin Cohn Ferris Glovsky and Popeo, P.C.

(57) ABSTRACT

Non-human animals comprising a human or humanized DPP4 nucleic acid sequence are provided. Non-human animals that comprise a replacement of the endogenous Dpp4 gene with a human or humanized DPP4 gene, or non-human animals comprising a human or humanized DPP4 gene in addition to the endogenous Dpp4 gene are described. Non-human animals comprising a human or humanized DPP4 gene under control of human or non-human DPP4 regulatory elements is also provided, including non-human animals that have a replacement of non-human Dpp4-encoding sequence with human DPP4-encoding sequence at an endogenous non-human Dpp4 locus. Non-human animals comprising human or humanized DPP4 gene sequences, wherein the non-human animals are rodents, e.g., mice or rats, are provided. Methods for making and using the non-human animals are described.

30 Claims, 19 Drawing Sheets

(56) References Cited

OTHER PUBLICATIONS

GenBank Accession No. KC776174.1, located at <http:www.ncbi.nlm.nih.gov/nuccore/KC776174.1>, last visited Aug. 10, 2015, 12 pages.

GenBank Accession No. JX869059.2 located at <http:www.ncbi.nlm.nih.gov/nuccore/JX869059.2>, last visited Aug. 10, 2015, 13 pages.

Gerich, J. (Dec. 4, 2013). "Pathogenesis and Management of Postpandrial Hyperglycemia: Role of Incretin-Based Therapies," *Intl. J. Gen. Med.* 6:877-895.

Lu, G. et al. (Aug. 8, 2013, e-published Jul. 7, 2013). "Molecular Basis of Binding Between Novel Human Coronavirus MERS-CoV and Its Receptor CD26," *Nature* 500(7461):227-231.

Page, C. et al. (Dec. 2012). "Induction of Alternatively Activated Macrophages Enhances Pathogenesis During Severe Acute Respiratory Syndrome Coronavirus Infection," *J Virol* 86(24):13334-13349.

Pascal, K.E. et al. (Jul. 14, 2015, e-published Jun. 29, 2015). "Pre- and Postexposure Efficacy of Fully Human Antibodies Against Spike Protein in a Novel Humanized Mouse Model of MERS-CoV Infection," *Proc. Natl. Acad. Sci. USA* 112(28):8738-8743.

Pascal, K.E. et al. (2015). "Supporting Information," *Proc. Natl. Acad. Sci. USA*, 10 pages.

Poueymirou, W.T. et al. (Jan. 2007, e-published Dec. 24, 2006). F0 Generation Mice Fully Derived From Gene-Targeted Embryonic Stem Cells Allowing Immediate Phenotypic Analyses, *Nat Biotechnol* 25(1):91-99.

Raj, V.S. et al. (Mar. 14, 2013). "Dipeptidyl Peptidase 4 is a Functional Receptor for the Emerging Human Coronavirus-EMC," *Nature* 495(7440):251-254.

Valenzuela, D.M. et al. (Jun. 2003, e-published May 5, 2003). High-Throughput Engineering of the Mouse Genome Coupled with High-Resolution Expression Analysis, *Nature Biotechnology* 21(6):652-659.

Zhao, J. et al. (Apr. 1, 2014). Rapid Generation of a Mouse Model for Middle East Respiratory Syndrome, *Proc. Natl. Acad. Sci. USA* 111(13):4970-4975.

Abbott, C.A. et al. (1994). "Genomic organization, exact localization, and tissue expression of the human CD26 (dipeptidyl peptidase IV) gene," *Immunogenetics* 40(5):331-338.

Bernard, A.M. et al. (Dec. 20, 1994). "Structure of the mouse dipeptidyl peptidase IV (CD26) gene," Biochemistry 33(50):15204-15214.

International Search Report mailed on Sep. 18, 2015, for PCT Application No. PCT/US2015/033024, filed May 28, 2015, 7 pages.

Reardon, S. (Jan. 30, 2014). "Biologists Make First Mouse Model for MERS," *Nature News* located at http://www.nature.com/news/biologists-make-first-mouse-model-for-mers-1.14634, last visited Sep. 8, 2015.

Simeoni, L. et al. (Sep. 2002). "Human CD26 expression in transgenic mice affects murine T-cell populations and modifies their subset distribution," *Human Immunology* 63(9):719-730.

Written Opinion mailed on Sep. 18, 2015, for PCT Application No. PCT/US2015/033024, filed May 28, 2015, 7 pages.

Center for Disease Control and Prevention (Oct. 4, 2012). "Severe Respiratory Illness Associated with a Novel Coronavirus—Saudi Arabia and Qatar, 2012," Morbidity and Mortality Weekly Report (MMWR), MMWR Early Release, located at <http://www.cdc.gov/mmwr/preview/mmwrhtml/mm6140a5.htm?s_cid=mm6140a5_w>, last visited on Apr. 23, 2016, 3 pages.

Gama Sosa, M.A. et al. (Mar. 2010, e-published Nov. 25, 2009). "Animal transgenesis: an overview," *Brain Struct Funct* 214(2-3):91-109.

Mulvihill, E.E. et al. (Dec. 2014, e-published Sep. 12, 2014). "Pharmacology, physiology, and mechanisms of action of dipeptidyl peptidase-4 inhibitors," *Endocr Rev* 35(6):992-1019.

Ristevski, S. (Feb. 2005). "Making better transgenic models: conditional, temporal, and spatial approaches," *Mol Biotechnol* 29(2):153-163.

Sigmund, C.D. (Jun. 2000). "Viewpoint: are studies in genetically altered mice out of control?" *Arterioscler Throm Vasc Biol* 20(6):1425-1429.

Smith, K.R. (Oct. 9, 2002). "Gene transfer in higher animals: theoretical considerations and key concepts," *J Biotechnol* 99(1):1-22.

Tong, C. et al. (Sep. 9, 2010). "Production of p53 gene knockout rats by homologous recombination in embryonic stem cells," *Nature* 467(7312):211-213.

Van Der Weyden L. et al. (Dec. 3, 2002, e-published Dec. 3, 2002). "Tools for targeted manipulation of the mouse genome," *Physiol Genomics* 11(3):133-164.

* cited by examiner

FIGURE 2

```
 ++
MKIPWKVLLG LLGAAALVTI ITVPVVLLNK GTDDATADSR KIYTLTDYLK NTYRLKLYSL
RWISDHEYLY KQENNILVEN AEYGNSSVFL ENSTFDEFGH SINDYSISPD GQFILLEYNY
VKQWRHSYTA SYDIYDLNKR QLITEERIPN NTQHYTWSPV GHKLAYVWNN DIYVKIEPNL
PSYRITWTGK EDIIYNGITD WVYEEEVFSA YSALWWSPNG TFLAYAQFND TEVPLIEYSF
YSDESLQYPK TVRVPYPKAG AVNPTVKFFV VNTDSLSSVT NATSIQITAP ASMLIGDHYL
CDVTWATDER ISLQWLRRIQ NYSVMDICDY DESSGRWNCL VARQHIEMST TGWVGRFRPS
EPHFTLDGNS FYKIISNEEG YRHICYFQID KKDCTFITKG TWEVIGIEAL TSDYLYYISN
EYKGMPGGRN LYKIQLSDYT KVTCLSCELN PERCQYYSVS FSKEAKYYQL RCSGPGLPLY
TLHSSVNDKG LRVLEDNSAL DKMLQNVQMP SKKLDFIILN ETKFWYQMIL PPHFDKSKKY
PLLLDVYAGP CSQKADTVFR LNWATYLAST ENIIVASFDG RGSGYQGDKI MHAINRRLGT
FEVEDQIEAA RQFSKMGFVD NKRIAINGWS YGGYVTSMVL GSGSGVFKCG IAVAPVSRWE
YYDSVYTERY MGLPTPEDNL DHYRNSTVMS RAENFKQVEY LLIHGTADDN VHFQQSAQIS
KALVDVGVDF QAMWYTDEDH GIASSTAHQH IYTHMSHFIK QCFSLP
```

+ Residues coded by mouse exon 1, are the same in human
Underscored residues coded by introduced human exons
Humanized protein sequence is 100% human

```
mDpp4  MKTPWKVLLGLLGVAALVTIIFVPIVLLSK--DEAAADSRRFYSLADYLKSIFRVKSYSIWWVSDFEYLYKQENNILLINAEHGNSSIFLENSTFESFGY
hDpp4  MKTPWKVLLGLLGAAALVTIIIVPVLLNKGTDDATADSRKTYTLTDYLKNTYRLKLYSIRWISDHEYLYKQENNILVNAEYGNSSVFLENSTFDEFGH mDpp4  ----HSVSPDRLFVLLEYNYVKQWRHSYTASYNIYDVNKRQLITEEKIPNNTQWITWSPEGHKLAYVWKNDIYVKVEPHLPSHRITSFGEENVIYNGITD
hDpp4  SINDYSISPDGQFILLEYNYVKQWRHSYTASYDIYDLNKRQLITEERIPNNTQWVTWSPVGHKLAYVWNNDIYVKIEPNLPSYRITWTGKEDIYNGITD mDpp4  WVYEEEVFGAYSALWWSPNNTFLAYAQFNDTGVPLIEYSFYSDESLQYPKTVWIPYPKAGAVNPTVKFFIVNIDSLSSSSAAPIQIPAPASVARGDHYL
hDpp4  WVYEEEVFSAYSALWWSPNGTFLAYAQFNDTEVPLIEYSFYSDESLQYPKTVRVPYPKAGAVNPTVKFFVVNTDSLSSVTNATSIQITAPASMLIGDHYL mDpp4  CDVVWATEERISLQWLRRIQNYSVMAICDYDKINLTWNCPSEQHVEMSTTGWVGREFRPAEPHFTSDGSSFYKIISDKDGYKHICHFPKDKDCTFITKG
hDpp4  CDVTWATQERISLQWLRRIQNYSVMDICDYDESSGRWNCLVARQHIEMSTTGWVGREFRPSEPHFTLDGNSFYKIISNEEGYRHICYFQIDKKDCTFITKG mDpp4  AWEVISIEALTSDYLYYISNQYKEMPGGRNLYKIQLTDHTNVKCLSCDLNPERCQYYAVSFSKEAKYYQLGCWGPGLPLYTLHRSTDHKELRVLEDNSAL
hDpp4  TWEVIGIEALTSDYLYYISNEYKGMPGGRNLYKIQLSDYTKVTCLSCELNPERCQYYSVSFSKEAKYYQLRCSGPGLPLYTLHSSVNDKGLRVLEDNSAL mDpp4  DRMLQDVQMPSKKLDFIVLNEARFWYQMILPPHFDKSKKYPLLLDVYAGPCSQKADASFRLNWATYLASTENIIVASFDGRGSGYQGDKIMHAINRRLGT
hDpp4  DKMLQNVQMPSKKLDFIILNETKFWYQMILPPHFDKSKKYPLLLDVYAGPCSQKADTVFRLNWATYLASTENIIVASFDGRGSGYQGDKIMHAINRRLGT mDpp4  LEVEDQIEAARQFVKNGFVDSKRVAIWGWSYGGYVTSMVLGSGSGVFKCGIAVAPVSRWEYYDSVYTERYMGLPIPEDNLDHYRNSTVMSRAEHFKQVEY
hDpp4  FEVEDQIEAARQFSKMGFVDNKRIAIWGWSYGGYVTSMVLGSGSGVFKCGIAVAPVSRWEYYDSVYTERYMGLPTPEDNLDHYRNSTVMSRAENFKQVEY mDpp4  LLIHGTADDNVHFQQSAQISKALVDAGVDFQAMWYTDEDHGIASSTAHQHIYSHMSHFLQQCFSLH
hDpp4  LLIHGTADDNVHFQQSAQISKALVDVGVDFQAMWYTDEDHGIASSTAHQHIYTHMSHFIKQCFSLP
```

FIGURE 8

| Human TaqMan Gain of allele assays | | | Human TaqMan Gain of allele assays | | |
|---|---|---|---|---|---|
| 7333 hTU | Fwd | TGGCTTATTCTATTCCTCACCTA (SEQ ID NO: 18) | 7333 | Fwd | TGCAGACTTGTCTTGACATTCATA (SEQ ID NO: 21) |
| | Probe (BHQ) | TGCTTCCCTCCTCCCTTCTGA (SEQ ID NO: 19) | | Probe (BHQ) | AGCCTCTGCAGACACAGGAATGGC (SEQ ID NO: 22) |
| | Rev | GGCCTTAGCCAGAAACTG (SEQ ID NO: 20) | | Rev | TCTGGGCACTGGTGTACTC (SEQ ID NO: 23) |

FIGURE 9

```
MKTPWKVLLG LLGAAALVTI ITVPVVLLNK GTDDATADSR KTYTLTDYLK NTYRLKLYSL
RWISDHEYLY KQENNILVFN AEYGNSSVFL ENSTFDEFGH SINDYSISPD GQFILLEYNY
VKQWRHSYTA SYDIYDLNKR QLITEERIPN NTQWVTWSPV GHKLAYVWNN DIYVKIEPNL
PSYRITWTGK EDIIYNGITD WVYEEVFSA YSALWWSPNG TFLAYAQFND TEVPLIEYSF
YSDESLQYPK TVRVPYPKAG AVNPTVKFFV VNTDSLSSVT NATSIQITAP ASMLIGDHYL
CDVTWATQER ISLQWLRRIQ NYSVMDICDY DESSGRWNCL VARQHIEMST TGWVGRFRPS
EPHFTLDGNS FYKIISNEEG YRHICYFQID KKDCTFITKG TWEVIGIEAL TSDYLYYISN
EYKGMPGGRN LYKIQLSDYT KVTCLSCELN PERCQYYSVS FSKEAKYYQL RCSGPGLPLY
TLHSSVNDKG LRVLEDNSAL DKMLQNVQMP SKKLDFIILN ETKFWYQMIL PPHFDKSKKY
PLILDVYAGP CSQKADTVFR LNWATYLAST ENIIVASFDG RGSGYQGDKI MHAINRRLGT
FEVEDQIEAA RQFSKMGFVD NKRIAIWGWS YGGYVTSMVL GSGSGVFKCG IAVAPVSRWE
YYDSVYTERY MGLPTPEDNL DHYRNSTVMS RAENFKQVEY LLIHGTADDN VHFQQSAQIS
KALVDGVDF QAMWYTDEDH GIASSTAHQH IYTHMSHFIK QCFSLP (SEQ ID NO: 24)
```

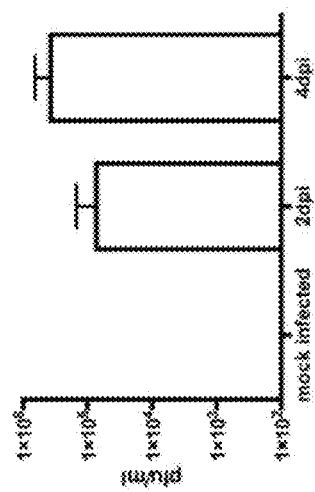
Figure 10A
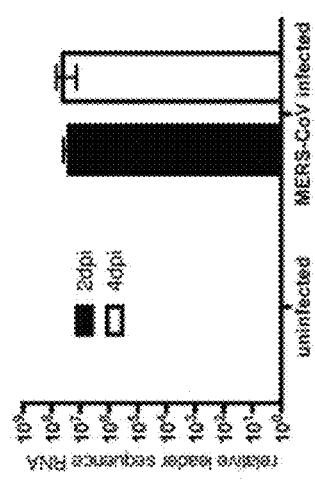
Figure 10B
Figure 10C
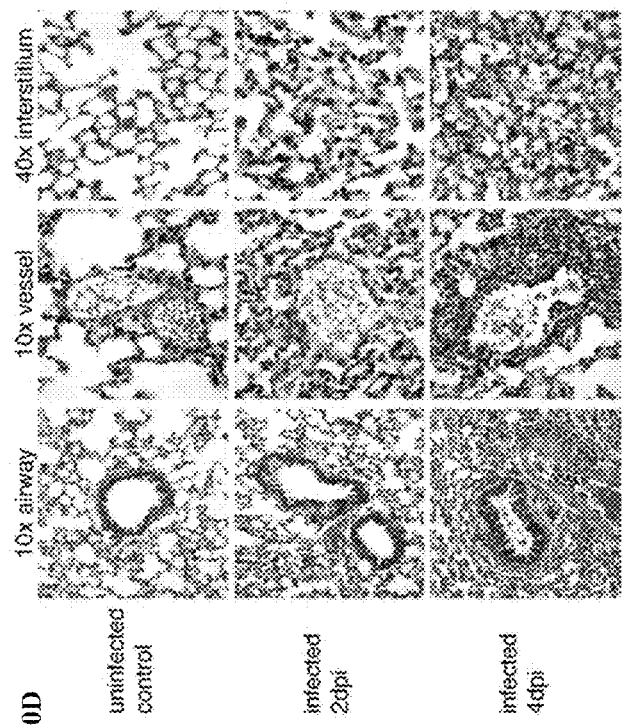
Figure 10D

FIGURE 17

SEQUENCE LISTING

```
<160> NUMBER OF SEQ ID NOS: 26

<210> SEQ ID NO 1
<211> LENGTH: 21
<212> TYPE: DNA
<213> ORGANISM: Artificial sequence
<220> FEATURE:
<223> OTHER INFORMATION: Synthetic construct

<400> SEQUENCE: 1
tcgccactgt gcctaacata g                                           21

<210> SEQ ID NO 2
<211> LENGTH: 22
<212> TYPE: DNA
<213> ORGANISM: Artificial sequence
<220> FEATURE:
<223> OTHER INFORMATION: Synthetic construct

<400> SEQUENCE: 2
ccgggactaa actggaacat tc                                          22

<210> SEQ ID NO 3
<211> LENGTH: 27
<212> TYPE: DNA
<213> ORGANISM: Artificial sequence
<220> FEATURE:
<223> OTHER INFORMATION: Synthetic construct

<400> SEQUENCE: 3
tcagtcaact tcttctgggt tgtttcc                                     27

<210> SEQ ID NO 4
<211> LENGTH: 22
<212> TYPE: DNA
<213> ORGANISM: Artificial sequence
<220> FEATURE:
<223> OTHER INFORMATION: Synthetic construct

<400> SEQUENCE: 4
```

```
cagctctggt ggagaactag ac                                           22

<210> SEQ ID NO 5
<211> LENGTH: 22
<212> TYPE: DNA
<213> ORGANISM: Artificial sequence
<220> FEATURE:
<223> OTHER INFORMATION: Synthetic construct

<400> SEQUENCE: 5
ggaggtcctc ggtctttaga ag                                           22

<210> SEQ ID NO 6
<211> LENGTH: 29
<212> TYPE: DNA
<213> ORGANISM: Artificial sequence
<220> FEATURE:
<223> OTHER INFORMATION: Synthetic construct

<400> SEQUENCE: 6
tcacacttag gcttataaac cattcccgt                                    29

<210> SEQ ID NO 7
<211> LENGTH: 20
<212> TYPE: DNA
<213> ORGANISM: Artificial sequence
<220> FEATURE:
<223> OTHER INFORMATION: Synthetic construct

<400> SEQUENCE: 7
gcggtctccc tcttctaacg                                              20

<210> SEQ ID NO 8
<211> LENGTH: 19
<212> TYPE: DNA
<213> ORGANISM: Artificial sequence
<220> FEATURE:
<223> OTHER INFORMATION: Synthetic construct

<400> SEQUENCE: 8
gcaagccgag cagatcaag                                               19

<210> SEQ ID NO 9
<211> LENGTH: 24
<212> TYPE: DNA
<213> ORGANISM: Artificial sequence
<220> FEATURE:
<223> OTHER INFORMATION: Synthetic construct

<400> SEQUENCE: 9
actcccacct gcaaatcctg ctgc                                         24

<210> SEQ ID NO 10
<211> LENGTH: 19
<212> TYPE: DNA
<213> ORGANISM: Artificial sequence
<220> FEATURE:
<223> OTHER INFORMATION: Synthetic construct

<400> SEQUENCE: 10
aaccgcactg gcatatgga                                               19

<210> SEQ ID NO 11
<211> LENGTH: 29
<212> TYPE: DNA
<213> ORGANISM: Artificial sequence
```

```
<220> FEATURE:
<223> OTHER INFORMATION: Synthetic construct

<400> SEQUENCE: 11
tacaaggtag tctgggatta ctaacaaaa                                    29

<210> SEQ ID NO 12
<211> LENGTH: 20
<212> TYPE: DNA
<213> ORGANISM: Artificial sequence
<220> FEATURE:
<223> OTHER INFORMATION: Synthetic construct

<400> SEQUENCE: 12
acatttatct agaaaggctc                                              20

<210> SEQ ID NO 13
<211> LENGTH: 158
<212> TYPE: DNA
<213> ORGANISM: Artificial sequence
<220> FEATURE:
<223> OTHER INFORMATION: Synthetic construct

<400> SEQUENCE: 13
aggagagaag ccaacaagat cataagatca tgctcagggc caaaattcaa gggcttctgc   60
cgtcgacggc cttagagaac tccaactggc gcactccaga cgccaccccc accccccagcc  120 cgcggtctcc ctcttctaac gcactcccac ctgcaaat                          158

<210> SEQ ID NO 14
<211> LENGTH: 160
<212> TYPE: DNA
<213> ORGANISM: Artificial sequence
<220> FEATURE:
<223> OTHER INFORMATION: Synthetic construct

<400> SEQUENCE: 14
ttattccagg gaactatgat gaggcttata taagaacgaa taagatcaga aatatcattc   60
tggcagttct tatggctcag ctcgagataa cttcgtataa tgtatgctat acgaagttat  120
atgcatggcc tccgcgccgg gttttggcgc ctcccgcggg                        160

<210> SEQ ID NO 15
<211> LENGTH: 160
<212> TYPE: DNA
<213> ORGANISM: Artificial sequence
<220> FEATURE:
<223> OTHER INFORMATION: Synthetic construct

<400> SEQUENCE: 15
atgtctggaa taacttcgta taatgtatgc tatacgaagt tatgctagta actataacgg   60
tcctaaggta gcgagctagc cagcatagct ctccatagct tatttaagac cacatttgtt  120
ctcattatct caaaagtgca ctgttaagat gaagatctta                        160

<210> SEQ ID NO 16
<211> LENGTH: 318
<212> TYPE: DNA
<213> ORGANISM: Artificial sequence
<220> FEATURE:
<223> OTHER INFORMATION: Synthetic construct

<400> SEQUENCE: 16
tattccaggg aactatgatg aggcttatat aagaacgaat aagatcagaa atatcattct   60
```

-continued

```
ggcagttctt atggctcagc tcgagataac ttcgtataat gtatgctata cgaagttatg      120
ctagtaacta taacggtcct aaggtagcga gctagccagc atagctctcc atagcttatt      180
taagaccaca tttgttctca ttatctcaaa agtgcactgt taagatgaag atcttaataa      240
tgttgcattg agacatttca ggctgctttc tccagtttta cacctgcaat cctaactaag      300
gatgcctgtc cccagaac                                                    318
```

<210> SEQ ID NO 17
<211> LENGTH: 766
<212> TYPE: PRT
<213> ORGANISM: Homo sapiens

<400> SEQUENCE: 17

```
Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

Leu Lys Asn Thr Tyr Arg Leu Lys Leu Tyr Ser Leu Arg Trp Ile Ser
    50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Val Phe
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Glu
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
    290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
```

-continued

```
            325                 330                 335
Trp Asn Cys Leu Val Ala Arg Gln His Ile Glu Met Ser Thr Thr Gly
            340                 345                 350
Trp Val Gly Arg Phe Arg Pro Ser Glu Pro His Phe Thr Leu Asp Gly
            355                 360                 365
Asn Ser Phe Tyr Lys Ile Ile Ser Asn Glu Glu Gly Tyr Arg His Ile
            370                 375                 380
Cys Tyr Phe Gln Ile Asp Lys Lys Asp Cys Thr Phe Ile Thr Lys Gly
385                 390                 395                 400
Thr Trp Glu Val Ile Gly Ile Glu Ala Leu Thr Ser Asp Tyr Leu Tyr
            405                 410                 415
Tyr Ile Ser Asn Glu Tyr Lys Gly Met Pro Gly Gly Arg Asn Leu Tyr
            420                 425                 430
Lys Ile Gln Leu Ser Asp Tyr Thr Lys Val Thr Cys Leu Ser Cys Glu
            435                 440                 445
Leu Asn Pro Glu Arg Cys Gln Tyr Tyr Ser Val Ser Phe Ser Lys Glu
            450                 455                 460
Ala Lys Tyr Tyr Gln Leu Arg Cys Ser Gly Pro Gly Leu Pro Leu Tyr
465                 470                 475                 480
Thr Leu His Ser Ser Val Asn Asp Lys Gly Leu Arg Val Leu Glu Asp
            485                 490                 495
Asn Ser Ala Leu Asp Lys Met Leu Gln Asn Val Gln Met Pro Ser Lys
            500                 505                 510
Lys Leu Asp Phe Ile Ile Leu Asn Glu Thr Lys Phe Trp Tyr Gln Met
            515                 520                 525
Ile Leu Pro Pro His Phe Asp Lys Ser Lys Lys Tyr Pro Leu Leu Leu
            530                 535                 540
Asp Val Tyr Ala Gly Pro Cys Ser Gln Lys Ala Asp Thr Val Phe Arg
545                 550                 555                 560
Leu Asn Trp Ala Thr Tyr Leu Ala Ser Thr Glu Asn Ile Ile Val Ala
            565                 570                 575
Ser Phe Asp Gly Arg Gly Ser Gly Tyr Gln Gly Asp Lys Ile Met His
            580                 585                 590
Ala Ile Asn Arg Arg Leu Gly Thr Phe Glu Val Glu Asp Gln Ile Glu
            595                 600                 605
Ala Ala Arg Gln Phe Ser Lys Met Gly Phe Val Asp Asn Lys Arg Ile
            610                 615                 620
Ala Ile Trp Gly Trp Ser Tyr Gly Gly Tyr Val Thr Ser Met Val Leu
625                 630                 635                 640
Gly Ser Gly Ser Gly Val Phe Lys Cys Gly Ile Ala Val Ala Pro Val
            645                 650                 655
Ser Arg Trp Glu Tyr Tyr Asp Ser Val Tyr Thr Glu Arg Tyr Met Gly
            660                 665                 670
Leu Pro Thr Pro Glu Asp Asn Leu Asp His Tyr Arg Asn Ser Thr Val
            675                 680                 685
Met Ser Arg Ala Glu Asn Phe Lys Gln Val Glu Tyr Leu Leu Ile His
            690                 695                 700
Gly Thr Ala Asp Asp Asn Val His Phe Gln Gln Ser Ala Gln Ile Ser
705                 710                 715                 720
Lys Ala Leu Val Asp Val Gly Val Asp Phe Gln Ala Met Trp Tyr Thr
            725                 730                 735
Asp Glu Asp His Gly Ile Ala Ser Ser Thr Ala His Gln His Ile Tyr
            740                 745                 750
```

Thr His Met Ser His Phe Ile Lys Gln Cys Phe Ser Leu Pro
        755                 760                 765

<210> SEQ ID NO 18
<211> LENGTH: 25
<212> TYPE: DNA
<213> ORGANISM: Artificial sequence
<220> FEATURE:
<223> OTHER INFORMATION: Synthetic construct

<400> SEQUENCE: 18
tggcttattc tctattcctc accta                                          25

<210> SEQ ID NO 19
<211> LENGTH: 22
<212> TYPE: DNA
<213> ORGANISM: Artificial sequence
<220> FEATURE:
<223> OTHER INFORMATION: Synthetic construct

<400> SEQUENCE: 19
tgctttccct cctcccttct ga                                             22

<210> SEQ ID NO 20
<211> LENGTH: 19
<212> TYPE: DNA
<213> ORGANISM: Artificial sequence
<220> FEATURE:
<223> OTHER INFORMATION: Synthetic construct

<400> SEQUENCE: 20
ggccttagcc cagaaactg                                                 19

<210> SEQ ID NO 21
<211> LENGTH: 24
<212> TYPE: DNA
<213> ORGANISM: Artificial sequence
<220> FEATURE:
<223> OTHER INFORMATION: Synthetic construct

<400> SEQUENCE: 21
tgcagacttg tcttgacatt cata                                           24

<210> SEQ ID NO 22
<211> LENGTH: 24
<212> TYPE: DNA
<213> ORGANISM: Artificial sequence
<220> FEATURE:
<223> OTHER INFORMATION: Synthetic construct

<400> SEQUENCE: 22
agcctctgca gacacaggaa tggc                                           24

<210> SEQ ID NO 23
<211> LENGTH: 19
<212> TYPE: DNA
<213> ORGANISM: Artificial sequence
<220> FEATURE:
<223> OTHER INFORMATION: Synthetic construct

<400> SEQUENCE: 23
tctgggcact ggtgtactc                                                 19

<210> SEQ ID NO 24
<211> LENGTH: 766

-continued

```
<212> TYPE: PRT
<213> ORGANISM: Homo sapiens

<400> SEQUENCE: 24

Met Lys Thr Pro Trp Lys Val Leu Leu Gly Leu Leu Ala Ala Ala
1               5                   10                  15

Leu Val Thr Ile Ile Thr Val Pro Val Val Leu Leu Asn Lys Gly Thr
                20                  25                  30

Asp Asp Ala Thr Ala Asp Ser Arg Lys Thr Tyr Thr Leu Thr Asp Tyr
            35                  40                  45

Leu Lys Asn Thr Tyr Arg Leu Lys Leu Tyr Ser Leu Arg Trp Ile Ser
50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Gly Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Glu Val Phe
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
    290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
            340                 345                 350

Trp Val Gly Arg Phe Arg Pro Ser Glu Pro His Phe Thr Leu Asp Gly
        355                 360                 365

Asn Ser Phe Tyr Lys Ile Ile Ser Asn Glu Glu Gly Tyr Arg His Ile
    370                 375                 380

Cys Tyr Phe Gln Ile Asp Lys Lys Asp Cys Thr Phe Ile Thr Lys Gly
385                 390                 395                 400
```

Thr Trp Glu Val Ile Gly Ile Glu Ala Leu Thr Ser Asp Tyr Leu Tyr
            405                 410                 415

Tyr Ile Ser Asn Glu Tyr Lys Gly Met Pro Gly Arg Asn Leu Tyr
        420                 425                 430

Lys Ile Gln Leu Ser Asp Tyr Thr Lys Val Thr Cys Leu Ser Cys Glu
            435                 440                 445

Leu Asn Pro Glu Arg Cys Gln Tyr Tyr Ser Val Ser Phe Ser Lys Glu
450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
                500                 505                 510

Lys Leu Asp Phe Ile Ile Leu Asn Glu Thr Lys Phe Trp Tyr Gln Met
            515                 520                 525

Ile Leu Pro Pro His Phe Asp Lys Ser Lys Lys Tyr Pro Leu Leu Leu
530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
                580                 585                 590

Ala Ile Asn Arg Arg Leu Gly Thr Phe Glu Val Glu Asp Gln Ile Glu
            595                 600                 605

Ala Ala Arg Gln Phe Ser Lys Met Gly Phe Val Asp Asn Lys Arg Ile
            610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
            660                 665                 670

Leu Pro Thr Pro Glu Asp Asn Leu Asp His Tyr Arg Asn Ser Thr Val
            675                 680                 685

Met Ser Arg Ala Glu Asn Phe Lys Gln Val Glu Tyr Leu Leu Ile His
            690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
            740                 745                 750

Thr His Met Ser His Phe Ile Lys Gln Cys Phe Ser Leu Pro
            755                 760                 765

<210> SEQ ID NO 25
<211> LENGTH: 760
<212> TYPE: PRT
<213> ORGANISM: Mus musculus

<400> SEQUENCE: 25

Met Lys Thr Pro Trp Lys Val Leu Leu Gly Leu Leu Gly Val Ala Ala

```
1               5                   10                  15
Leu Val Thr Ile Ile Thr Val Pro Ile Val Leu Leu Ser Lys Asp Glu
                    20                  25                  30

Ala Ala Ala Asp Ser Arg Arg Thr Tyr Ser Leu Ala Asp Tyr Leu Lys
                35                  40                  45

Ser Thr Phe Arg Val Lys Ser Tyr Ser Leu Trp Trp Val Ser Asp Phe
            50                  55                  60

Glu Tyr Leu Tyr Lys Gln Glu Asn Asn Ile Leu Leu Asn Ala Glu
65                  70                  75                  80

His Gly Asn Ser Ser Ile Phe Leu Glu Asn Ser Thr Phe Glu Ser Phe
                    85                  90                  95

Gly Tyr His Ser Val Ser Pro Asp Arg Leu Phe Val Leu Leu Glu Tyr
                100                 105                 110

Asn Tyr Val Lys Gln Trp Arg His Ser Tyr Thr Ala Ser Tyr Asn Ile
            115                 120                 125

Tyr Asp Val Asn Lys Arg Gln Leu Ile Thr Glu Glu Lys Ile Pro Asn
130                 135                 140

Asn Thr Gln Trp Ile Thr Trp Ser Pro Glu Gly His Lys Leu Ala Tyr
145                 150                 155                 160

Val Trp Lys Asn Asp Ile Tyr Val Lys Val Glu Pro His Leu Pro Ser
                165                 170                 175

His Arg Ile Thr Ser Thr Gly Glu Glu Asn Val Ile Tyr Asn Gly Ile
                180                 185                 190

Thr Asp Trp Val Tyr Glu Glu Glu Val Phe Gly Ala Tyr Ser Ala Leu
            195                 200                 205

Trp Trp Ser Pro Asn Asn Thr Phe Leu Ala Tyr Ala Gln Phe Asn Asp
210                 215                 220

Thr Gly Val Pro Leu Ile Glu Tyr Ser Phe Tyr Ser Asp Glu Ser Leu
225                 230                 235                 240

Gln Tyr Pro Lys Thr Val Trp Ile Pro Tyr Pro Lys Ala Gly Ala Val
                245                 250                 255

Asn Pro Thr Val Lys Phe Phe Ile Val Asn Ile Asp Ser Leu Ser Ser
                260                 265                 270

Ser Ser Ser Ala Ala Pro Ile Gln Ile Pro Ala Pro Ala Ser Val Ala
            275                 280                 285

Arg Gly Asp His Tyr Leu Cys Asp Val Val Trp Ala Thr Glu Glu Arg
290                 295                 300

Ile Ser Leu Gln Trp Leu Arg Arg Ile Gln Asn Tyr Ser Val Met Ala
305                 310                 315                 320

Ile Cys Asp Tyr Asp Lys Ile Asn Leu Thr Trp Asn Cys Pro Ser Glu
                325                 330                 335

Gln Gln His Val Glu Met Ser Thr Thr Gly Trp Val Gly Arg Phe Arg
                340                 345                 350

Pro Ala Glu Pro His Phe Thr Ser Asp Gly Ser Ser Phe Tyr Lys Ile
            355                 360                 365

Ile Ser Asp Lys Asp Gly Tyr Lys His Ile Cys His Phe Pro Lys Asp
370                 375                 380

Lys Lys Asp Cys Thr Phe Ile Thr Lys Gly Ala Trp Glu Val Ile Ser
385                 390                 395                 400

Ile Glu Ala Leu Thr Ser Asp Tyr Leu Tyr Tyr Ile Ser Asn Gln Tyr
                405                 410                 415

Lys Glu Met Pro Gly Gly Arg Asn Leu Tyr Lys Ile Gln Leu Thr Asp
                420                 425                 430
```

```
His Thr Asn Val Lys Cys Leu Ser Cys Asp Leu Asn Pro Glu Arg Cys
            435                 440                 445

Gln Tyr Tyr Ala Val Ser Phe Ser Lys Glu Ala Lys Tyr Tyr Gln Leu
    450                 455                 460

Gly Cys Trp Gly Pro Gly Leu Pro Leu Tyr Thr Leu His Arg Ser Thr
465                 470                 475                 480

Asp His Lys Glu Leu Arg Val Leu Glu Asp Asn Ser Ala Leu Asp Arg
                485                 490                 495

Met Leu Gln Asp Val Gln Met Pro Ser Lys Lys Leu Asp Phe Ile Val
            500                 505                 510

Leu Asn Glu Thr Arg Phe Trp Tyr Gln Met Ile Leu Pro Pro His Phe
        515                 520                 525

Asp Lys Ser Lys Lys Tyr Pro Leu Leu Leu Asp Val Tyr Ala Gly Pro
    530                 535                 540

Cys Ser Gln Lys Ala Asp Ala Ser Phe Arg Leu Asn Trp Ala Thr Tyr
545                 550                 555                 560

Leu Ala Ser Thr Glu Asn Ile Ile Val Ala Ser Phe Asp Gly Arg Gly
                565                 570                 575

Ser Gly Tyr Gln Gly Asp Lys Ile Met His Ala Ile Asn Arg Arg Leu
            580                 585                 590

Gly Thr Leu Glu Val Glu Asp Gln Ile Glu Ala Ala Arg Gln Phe Val
        595                 600                 605

Lys Met Gly Phe Val Asp Ser Lys Arg Val Ala Ile Trp Gly Trp Ser
    610                 615                 620

Tyr Gly Gly Tyr Val Thr Ser Met Val Leu Gly Ser Gly Ser Gly Val
625                 630                 635                 640

Phe Lys Cys Gly Ile Ala Val Ala Pro Val Ser Arg Trp Glu Tyr Tyr
                645                 650                 655

Asp Ser Val Tyr Thr Glu Arg Tyr Met Gly Leu Pro Ile Pro Glu Asp
            660                 665                 670

Asn Leu Asp His Tyr Arg Asn Ser Thr Val Met Ser Arg Ala Glu His
        675                 680                 685

Phe Lys Gln Val Glu Tyr Leu Leu Ile His Gly Thr Ala Asp Asp Asn
    690                 695                 700

Val His Phe Gln Gln Ser Ala Gln Ile Ser Lys Ala Leu Val Asp Ala
705                 710                 715                 720

Gly Val Asp Phe Gln Ala Met Trp Tyr Thr Asp Glu Asp His Gly Ile
                725                 730                 735

Ala Ser Ser Thr Ala His Gln His Ile Tyr Ser His Met Ser His Phe
            740                 745                 750

Leu Gln Gln Cys Phe Ser Leu His
        755                 760

<210> SEQ ID NO 26
<211> LENGTH: 766
<212> TYPE: PRT
<213> ORGANISM: Homo sapiens

<400> SEQUENCE: 26

Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
                20                  25                  30

Asp Asp Ala Thr Ala Asp Ser Arg Lys Thr Tyr Thr Leu Thr Asp Tyr
```

```
                35                  40                  45
Leu Lys Asn Thr Tyr Arg Leu Lys Leu Tyr Ser Leu Arg Trp Ile Ser
 50                  55                  60
Asp His Glu Tyr Leu Tyr Lys Gln Glu Asn Asn Ile Leu Val Phe Asn
 65                  70                  75                  80
Ala Glu Tyr Gly Asn Ser Ser Val Phe Leu Glu Asn Ser Thr Phe Asp
                 85                  90                  95
Glu Phe Gly His Ser Ile Asn Asp Tyr Ser Ile Ser Pro Asp Gly Gln
                100                 105                 110
Phe Ile Leu Leu Glu Tyr Asn Tyr Val Lys Gln Trp Arg His Ser Tyr
            115                 120                 125
Thr Ala Ser Tyr Asp Ile Tyr Asp Leu Asn Lys Arg Gln Leu Ile Thr
        130                 135                 140
Glu Glu Arg Ile Pro Asn Asn Thr Gln Trp Val Thr Trp Ser Pro Val
145                 150                 155                 160
Gly His Lys Leu Ala Tyr Val Trp Asn Asn Asp Ile Tyr Val Lys Ile
                165                 170                 175
Glu Pro Asn Leu Pro Ser Tyr Arg Ile Thr Trp Thr Gly Lys Glu Asp
            180                 185                 190
Ile Ile Tyr Asn Gly Ile Thr Asp Trp Val Tyr Glu Glu Glu Val Phe
        195                 200                 205
Ser Ala Tyr Ser Ala Leu Trp Trp Ser Pro Asn Gly Thr Phe Leu Ala
210                 215                 220
Tyr Ala Gln Phe Asn Asp Thr Glu Val Pro Leu Ile Glu Tyr Ser Phe
225                 230                 235                 240
Tyr Ser Asp Glu Ser Leu Gln Tyr Pro Lys Thr Val Arg Val Pro Tyr
                245                 250                 255
Pro Lys Ala Gly Ala Val Asn Pro Thr Val Lys Phe Phe Val Val Asn
            260                 265                 270
Thr Asp Ser Leu Ser Ser Val Thr Asn Ala Thr Ser Ile Gln Ile Thr
        275                 280                 285
Ala Pro Ala Ser Met Leu Ile Gly Asp His Tyr Leu Cys Asp Val Thr
    290                 295                 300
Trp Ala Thr Gln Glu Arg Ile Ser Leu Gln Trp Leu Arg Arg Ile Gln
305                 310                 315                 320
Asn Tyr Ser Val Met Asp Ile Cys Asp Tyr Asp Glu Ser Ser Gly Arg
                325                 330                 335
Trp Asn Cys Leu Val Ala Arg Gln His Ile Glu Met Ser Thr Thr Gly
            340                 345                 350
Trp Val Gly Arg Phe Arg Pro Ser Glu Pro His Phe Thr Leu Asp Gly
        355                 360                 365
Asn Ser Phe Tyr Lys Ile Ile Ser Asn Glu Glu Gly Tyr Arg His Ile
    370                 375                 380
Cys Tyr Phe Gln Ile Asp Lys Lys Asp Cys Thr Phe Ile Thr Lys Gly
385                 390                 395                 400
Thr Trp Glu Val Ile Gly Ile Glu Ala Leu Thr Ser Asp Tyr Leu Tyr
                405                 410                 415
Tyr Ile Ser Asn Glu Tyr Lys Gly Met Pro Gly Gly Arg Asn Leu Tyr
            420                 425                 430
Lys Ile Gln Leu Ser Asp Tyr Thr Lys Val Thr Cys Leu Ser Cys Glu
        435                 440                 445
Leu Asn Pro Glu Arg Cys Gln Tyr Tyr Ser Val Ser Phe Ser Lys Glu
    450                 455                 460
```

```
Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
            500                 505                 510

Lys Leu Asp Phe Ile Ile Leu Asn Glu Thr Lys Phe Trp Tyr Gln Met
            515                 520                 525

Ile Leu Pro Pro His Phe Asp Lys Ser Lys Lys Tyr Pro Leu Leu Leu
        530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
            580                 585                 590

Ala Ile Asn Arg Arg Leu Gly Thr Phe Glu Val Glu Asp Gln Ile Glu
            595                 600                 605

Ala Ala Arg Gln Phe Ser Lys Met Gly Phe Val Asp Asn Lys Arg Ile
    610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
            660                 665                 670

Leu Pro Thr Pro Glu Asp Asn Leu Asp His Tyr Arg Asn Ser Thr Val
            675                 680                 685

Met Ser Arg Ala Glu Asn Phe Lys Gln Val Glu Tyr Leu Leu Ile His
    690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
            740                 745                 750

Thr His Met Ser His Phe Ile Lys Gln Cys Phe Ser Leu Pro
            755                 760                 765
```

HUMANIZED DIPEPTIDYL PEPTIDASE IV (DPP4) ANIMALS

CROSS-REFERENCE TO RELATED APPLICATIONS

This application claims priority to U.S. Provisional Patent Application No. 62/005,476, filed May 30, 2014, U.S. Provisional Patent Application No. 62/051,626, filed Sep. 17, 2014, and U.S. Provisional Patent Application No. 62/072,692, filed Oct. 30, 2014, the disclosures of each of which are incorporated by reference herein in their entireties.

INCORPORATION BY REFERENCE

The content of the following submission on ASCII text file is incorporated herein by reference in its entirety: a computer readable form (CFR) of the Sequence Listing (file name: 47206501001US_Sequence_Listing, date created: Aug. 7, 2015, size: 31,762 bytes).

FIELD OF INVENTION

Non-human animals comprising nucleic acid sequences encoding a dipeptidyl peptidase IV (DPP4) protein that comprise a human sequence. Transgenic non-human animals comprising a DPP4 gene that is human in whole or in part. Non-human animals that express human or humanized DPP4 proteins. Methods for making and using non-human animals comprising human or humanized DPP4 nucleic acid sequences.

BACKGROUND

Dipeptidyl peptidase IV (DPP4) is a therapeutic target for the treatment of a variety of human diseases, disorders and conditions, including, for example, hyperglycemia (see, e.g., Gerich (2013) Pathogenesis and Management of Postpandrial Hyperglycemia: Role of Incretin-Based Therapies, Intl. J. Gen. Med. 6:877-895) and Middle East respiratory syndrome coronavirus (MERS-CoV) infection (see, e.g., Raj et al. (2013) Dipeptidyl Peptidase 4 is a Functional Receptor for the Emerging Human Coronovirus-EMC, Nature 495 (7440):251-254).

The evaluation of the pharmacokinetics (PK) and pharmacodynamics (PD) of therapeutic molecules that specifically target human DPP4 protein are routinely performed in non-human animals, e.g., rodents, e.g., mice or rats. However, the PD of such molecules cannot properly be determined in certain non-human animals if these therapeutic molecules also do not target the endogenous Dpp4 protein.

Moreover, the evaluation of the in vivo therapeutic efficacy of human DPP4-specific small molecule, peptide or protein (i.e., biologic) antagonists in non-human animal models of diseases is problematic in certain non-human animals in which the species-specific antagonist does not interact with the endogenous Dpp4 protein. Furthermore, the evaluation of the in vivo therapeutic efficacy of small molecule, peptide or protein (i.e., biologic) antagonists that target molecules that specifically interact with human DPP4 protein is also problematic in certain non-human animals in which the therapeutic target molecule itself does not interact with the endogenous Dpp4 protein.

Accordingly, there is a need for non-human animals, e.g., rodents, e.g., mice or rats that comprise a human or humanized DPP4 gene. For example, there is a need for non-human animals, e.g., rodents, e.g., mice or rats, in which the Dpp4 gene of the non-human animal is humanized in whole or in part or replaced (e.g., at the endogenous non-human loci) with a human DPP4 gene comprising sequences encoding human or humanized DPP4 protein.

There is also a need for non-human animals comprising a DPP4 gene (e.g., human or humanized) in which the DPP4 gene is under control of non-human regulatory elements (e.g., endogenous regulatory elements), for example, in the 5' flanking region, e.g., promoter and enhancer(s), or in the 3' untranslated region, of the DPP4 gene.

There is also a need for non-human animals comprising a DPP4 gene (e.g., human or humanized) in which the DPP4 gene is under control of human regulatory elements, for example, in the 5' flanking region, e.g., promoter or enhancer(s), or in the 3' untranslated region, of the human DPP4 gene.

There is also a need for humanized non-human animals that express human or humanized DPP4 protein on the surface of immune cells, e.g., T cells, and/or on the surface of cells in one or more tissues, e.g., placenta, kidney, lung, liver, skeletal muscle, heart, brain and/or pancreas, at a level similar to that of Dpp4 protein on the surface of immune cells, e.g., T cells, and/or on the surface of cells in one or more tissues, e.g., placenta, kidney, lung, liver, skeletal muscle, heart, brain and/or pancreas, of an age-matched non-human animal that expresses functional Dpp4 protein, but does not comprise the human or humanized DPP4 gene.

In addition, there is a need for humanized non-human animals that express human or humanized DPP4 protein on the surface of immune cells, e.g., T cells, and/or on the surface of cells in one or more tissues, e.g., placenta, kidney, lung, liver, skeletal muscle, heart, brain and/or pancreas, at a level higher than or lower than that of Dpp4 protein on the surface of immune cells, e.g., T cells, and/or on the surface of cells in one or more tissues, e.g., placenta, kidney, lung, liver, skeletal muscle, heart, brain and/or pancreas, of an age-matched non-human animal that expresses functional Dpp4 protein, but does not comprise the human or humanized DPP4 gene.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

SUMMARY

Non-human animals comprising nucleic acid sequences encoding a DPP4 protein that comprises a human sequence are provided.

Transgenic non-human animals comprising a DPP4 gene that is human in whole or in part are provided.

Non-human animals that express human or humanized DPP4 protein are provided.

Non-human animals having a replacement (in whole or in part) of the endogenous non-human animal Dpp4 gene are provided.

Non-human animals comprising a DPP4 humanization (in whole or in part) at an endogenous non-human Dpp4 locus are provided.

Non-human animals are provided that have a human or humanized DPP4 gene, wherein the non-human animals do not express endogenous Dpp4 protein, and wherein the non-human animals express human or humanized DPP4 protein on the surface of immune cells, e.g., T cells, and/or on the surface of cells in one or more tissues, including placenta, kidney, lung, liver, skeletal muscle, heart, brain and/or pancreas, at a level similar to that of Dpp4 protein present on the surface of immune cells, e.g., T cells, and/or on the surface of cells in one or more tissues, including placenta, kidney, lung, liver, skeletal muscle, heart, brain and/or pancreas, of an age-matched non-human animal that expresses functional endogenous Dpp4 protein, but does not comprise the replacement.

In one aspect, non-human animals comprising a human or humanized DPP4 nucleic acid sequence are provided.

In one aspect, genetically modified non-human animals are provided that comprise a replacement at an endogenous Dpp4 locus of a gene encoding an endogenous Dpp4 gene encoding a human or humanized DPP4 protein. Rodents, e.g., mice or rats, are provided that comprise a replacement of an endogenous Dpp4 gene, at an endogenous Dpp4 locus, with a human Dpp4 gene. In one embodiment, the rodent is heterozygous for a replacement at an endogenous Dpp4 locus of an endogenous Dpp4 gene encoding a human or humanized DPP4 protein. In one embodiment, the rodent is homozygous for a replacement at an endogenous Dpp4 locus of an endogenous Dpp4 gene encoding a human or humanized DPP4 protein. In one embodiment, the rodent is a mouse. In one embodiment, the rodent is a rat.

In one aspect, genetically modified rodents, e.g., mice or rats, are provided comprising a humanization of an endogenous rodent Dpp4 gene, wherein the humanization comprises a replacement at the endogenous rodent Dpp4 locus of a rodent gene encoding an exon of an Dpp4 gene with a nucleic acid sequence encoding at least one exon of a human DPP4 gene to form a modified DPP4 gene, wherein expression of the modified DPP4 gene is under control of rodent regulatory elements at the endogenous rodent Dpp4 locus.

In one embodiment, the rodent is heterozygous for the nucleic acid sequence encoding at least one exon of a human DPP4 gene to form a modified DPP4 gene. In one embodiment, the rodent is homozygous for the nucleic acid sequence encoding at least one exon of a human DPP4 gene to form a modified DPP4 gene.

In one embodiment, the rodent is a mouse or a rat. In one embodiment, the rodent is a mouse. In one embodiment, the rodent is a rat.

In one embodiment, the human DPP4 gene encoding a human or humanized DPP4 protein comprises exon 2 through exon 26 of the human DPP4 gene.

In one embodiment, the humanized DPP4 protein comprises the extracellular domain of the human DPP4 protein.

In one embodiment, the humanized DPP4 protein comprises the transmembrane domain and cytoplasmic domain of the mouse Dpp4 protein.

In one embodiment, the rodent is a mouse that is incapable of expressing a mouse Dpp4 protein.

In one embodiment, the rodent is a mouse wherein a contiguous genomic fragment of mouse Dpp4 sequence encoding exon 2 through exon 26 of mouse Dpp4 is replaced with a contiguous genomic fragment of human DPP4 sequence encoding exon 2 through exon 26 of human DPP4.

In one aspect, genetically modified rodents, e.g., a mouse or rat, are provided that express a human or humanized DPP4 protein, wherein the rodent that expresses a human or humanized DPP4 protein comprises a normal immune system, i.e., the number of immune cells, e.g., T cells, in the blood, plasma or serum of the rodent expressing human or humanized DPP4 protein are similar to the number of immune cells, e.g., T cells, in the blood, plasma or serum of a rodent that expresses functional endogenous Dpp4 protein. In one embodiment, the rodent is a mouse. In one embodiment, the rodent is a rat.

In one embodiment, the blood of the rodent that expresses a human or humanized DPP4 protein has approximately the same number of immune cells, e.g., T cells, as a rodent that expresses a functional, endogenous Dpp4 protein, e.g., a wild-type mouse or rat. In one embodiment, the rodent is a mouse. In one embodiment, the rodent is a rat.

In one embodiment, the mouse expressing human or humanized DPP4 on the surface of T cells has an amount of T cells present in the blood of at least about 20%, 30%, 40%, 50%, 60%, 70%, 80%, 90%, 100%, 110%, 120%, 130%, 140%, 150%, 160%, 170%, 180%, 190% or 200% of the amount of T cells present in the blood of an age-matched mouse that expresses functional endogenous Dpp4 protein, but does not comprise a replacement of an endogenous Dpp4 gene, at an endogenous mouse Dpp4 locus, with a human DPP4 gene.

In one embodiment, the mouse expressing human or humanized DPP4 protein on the surface of T cells has an amount of T cells in the blood of between about 20% and about 200%, between about 40% and about 160%, or between about 80% and about 120% of the amount of T cells present in the blood of an age-matched mouse that expresses functional endogenous Dpp4 protein, but does not comprise a replacement of an endogenous Dpp4 gene, at an endogenous mouse Dpp4 locus, with a human DPP4 gene.

In one aspect, genetically modified rodents, e.g., a mouse or rat, are provided that express a human or humanized DPP4 protein, wherein the rodent expresses a human or humanized DPP4 protein on the surface of immune cells, e.g., T cells, and/or on the surface of cells in one or more tissues, e.g., placenta, kidney, lung, liver, skeletal muscle, heart, brain and/or pancreas, of an age-matched rodent that expresses functional endogenous Dpp4 protein. In one embodiment, the rodent is a mouse. In one embodiment, the rodent is a rat.

In one embodiment, the immune cells, e.g., T cells, of the rodent that expresses a human or humanized DPP4 protein have approximately the same level of DPP4 protein on its surface as the immune cells, e.g., T cells, of a rodent that expresses a functional, endogenous Dpp4 protein, e.g., a wild-type mouse or rat. In one embodiment, the rodent is a mouse. In one embodiment, the rodent is a rat.

In one embodiment, the mouse expresses human or humanized DPP4 protein on the surface of immune cells, e.g., T cells, at a level of at least about 20%, 30%, 40%, 50%, 60%, 70%, 80%, 90%, 100%, 110%, 120%, 130%, 140%, 150%, 160%, 170%, 180%, 190% or 200% of the level of Dpp4 protein on the surface of immune cells, e.g., T cells, of an age-matched mouse that expresses functional endogenous Dpp4 protein, but does not comprise a replacement of an endogenous Dpp4 gene, at an endogenous mouse Dpp4 locus, with a human DPP4 gene.

In one embodiment, the mouse expresses human or humanized DPP4 protein on the surface of immune cells, e.g., T cells, at a level of between about 20% and about 200%, between about 40% and about 160%, or between about 80% and about 120% of the level of mouse Dpp4 protein present on the surface of immune cells, e.g., T cells, of an age-matched mouse that expresses functional endogenous Dpp4 protein, but does not comprise a replacement of an endogenous Dpp4 gene, at an endogenous mouse Dpp4 locus, with a human DPP4 gene.

In one embodiment, the cells in one or more tissues, e.g., placenta, kidney, lung, liver, skeletal muscle, heart, brain and/or pancreas, of the rodent that expresses a human or humanized DPP4 protein have approximately the same level of DPP4 protein on its surface as the cells in one or more tissues, e.g., placenta, kidney, lung, liver, skeletal muscle, heart, brain and/or pancreas, of a rodent that expresses a functional, endogenous Dpp4 protein, e.g., a wild-type mouse or rat. In one embodiment, the rodent is a mouse. In one embodiment, the rodent is a rat.

In one embodiment, the mouse expresses human or humanized DPP4 protein on the surface of cells in one or more tissues, e.g., placenta, kidney, lung, liver, skeletal muscle, heart, brain and/or pancreas, at a level of at least about 20%, 30%, 40%, 50%, 60%, 70%, 80%, 90%, 100%, 110%, 120%, 130%, 140%, 150%, 160%, 170%, 180%, 190% or 200% of the level of Dpp4 protein on the surface of cells in one or more tissues, e.g., placenta, kidney, lung, liver, skeletal muscle, heart, brain and/or pancreas, of an age-matched mouse that expresses functional endogenous Dpp4 protein, but does not comprise a replacement of an endogenous Dpp4 gene, at an endogenous mouse Dpp4 locus, with a human DPP4 gene.

In one embodiment, the mouse expresses human or humanized DPP4 protein on the surface of cells in one or more tissues, e.g., placenta, kidney, lung, liver, skeletal muscle, heart, brain and/or pancreas, at a level of between about 20% and about 200%, between about 40% and about 160%, or between about 80% and about 120% of the level of mouse Dpp4 protein present on the surface of cells in one or more tissues, e.g., placenta, kidney, lung, liver, skeletal muscle, heart, brain and/or pancreas, of an age-matched mouse that expresses functional endogenous Dpp4 protein, but does not comprise a replacement of an endogenous Dpp4 gene, at an endogenous mouse Dpp4 locus, with a human DPP4 gene.

In one aspect, a genetically modified rodent is provided, comprising a humanized DPP4 gene comprising a replacement of rodent Dpp4 extracellular domain-encoding sequence with human DPP4 extracellular domain-coding sequence, wherein the humanized DPP4 gene comprises a rodent Dpp4 transmembrane sequence and a rodent Dpp4 cytoplasmic sequence, wherein the humanized DPP4 gene is under control of endogenous rodent Dpp4 regulatory elements at the endogenous Dpp4 locus.

In one embodiment, the rodent is heterozygous for the humanized DPP4 gene. In one embodiment, the rodent is homozygous for the humanized DPP4 gene.

In one embodiment, the rodent is a mouse or a rat. In one embodiment, the rodent is a mouse. In one embodiment, the rodent is a rat.

In one embodiment, the mouse is incapable of expressing a mouse Dpp4 protein.

In one embodiment, the rodent regulatory elements or sequences at the endogenous rodent Dpp4 locus are from a mouse or a rat.

In one embodiment, the rodent regulatory elements or sequences are endogenous rodent regulatory elements or sequences at the rodent Dpp4 locus are from a mouse or a rat.

In one aspect, a non-human animal, e.g., a rodent, e.g., a mouse or rat, is provided that expresses human or humanized DPP4 protein, wherein the non-human animal expresses human or humanized DPP4 protein from an endogenous non-human Dpp4 locus. In an embodiment, the non-human animal is a rodent. In an embodiment, the rodent is a mouse. In an embodiment, the rodent is a rat. In one embodiment, the rodent is heterozygous for the endogenous non-human Dpp4 locus expressing a human or humanized DPP4 protein. In one embodiment, the rodent is homozygous for the endogenous non-human Dpp4 locus expressing a human or humanized DPP4 protein.

In one aspect, a genetically modified mouse is provided that expresses human or humanized DPP4 protein from an endogenous mouse Dpp4 locus, wherein the endogenous mouse Dpp4 gene has been replaced, in whole or in part, with a human DPP4 gene.

In one embodiment, about 78.8 kb at the endogenous mouse Dpp4 locus, including exon 2 through the stop codon in exon 26, is deleted and replaced with about 81.8 kb of human DPP4 gene sequence comprising exon 2 through exon 26 and a portion of the 3' untranslated sequence of the human DPP4 gene. In a specific embodiment, the human DPP4 gene comprises exon 2 through exon 26 and a portion of the 3' untranslated sequence of the human DPP4 gene of human BAC RP11-68L22. In a specific embodiment, the DPP4 gene comprises mouse Dpp4 gene 5' regulatory elements, mouse Dpp4 exon 1, including the first two amino acids, Met and Lys, of the mouse Dpp4 protein, and mouse Dpp4 3' regulatory elements (e.g., 3' untranslated region), and human DPP4 gene exon 2 through exon 26, i.e., the human DPP4 protein coding sequences, except for the first two amino acids, which are derived from mouse Dpp4 exon 1.

In one aspect, a genetically modified mouse is provided that comprises a nucleotide sequence encoding a human or humanized DPP4 protein, wherein the nucleotide sequence encoding the human or humanized DPP4 protein replaces, in whole or in part, an endogenous nucleotide sequence encoding an endogenous mouse Dpp4 protein.

In one embodiment, the mouse is heterozygous for the nucleotide sequence encoding a human or humanized DPP4 protein. In one embodiment, the mouse is homozygous for the nucleotide sequence encoding a human or humanized DPP4 protein.

In one aspect, a method is provided for making a humanized DPP4 rodent, comprising replacing a rodent Dpp4 gene sequence encoding rodent Dpp4 protein with a human DPP4 gene sequence comprising one or more exons of the human DPP4 gene sequence encoding human or humanized DPP4 protein, wherein the replacement is at an endogenous rodent Dpp4 locus and the human DPP4 gene sequence comprising one or more exons of the human DPP4 gene sequence encoding human or humanized DPP4 protein is operably linked to rodent regulatory elements or sequences at the endogenous rodent Dpp4 locus.

In one embodiment, the rodent is heterozygous for the nucleotide sequence encoding a human or humanized DPP4 protein. In one embodiment, the rodent is homozygous for the nucleotide sequence encoding a human or humanized DPP4 protein.

In one embodiment, the rodent is a mouse or a rat. In one embodiment, the rodent is a mouse. In one embodiment, the rodent is a rat.

In one embodiment, the rodent regulatory elements or sequences are derived from a mouse. In one embodiment, the rodent regulatory elements or sequences are derived from a rat.

In one embodiment, the rodent regulatory elements or sequences are endogenous rodent regulatory elements or sequences at the rodent Dpp4 locus. In one embodiment, the rodent is a mouse. In one embodiment, the rodent is a rat.

In one embodiment, the human DPP4 gene sequence replacing the rodent Dpp4 gene sequence comprises at least one exon of the human DPP4 gene sequence. In other embodiments, the human DPP4 gene sequence replacing the rodent Dpp4 gene sequence comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 exons of the human DPP4 gene sequence. In one embodiment, the human DPP4 gene sequence replacing the rodent Dpp4 gene sequence comprises all 26 exons of the human DPP4 gene sequence. In one embodiment, the rodent is a mouse. In one embodiment, the rodent is a rat.

In one embodiment, the human or humanized DPP4 gene sequence replacing the rodent Dpp4 gene sequence encodes a protein that is about 85%, 90%, 95%, 96%, 97%, 98%, or about 99% identical to a human DPP4.

In one embodiment, the human or humanized DPP4 gene sequence replacing the rodent Dpp4 gene sequence comprises at least one exon of the human DPP4 gene sequence encoding the extracellular domain of the human DPP4 protein. In other embodiments, the human DPP4 gene sequence replacing the rodent Dpp4 gene sequence comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, or at least 23 exons of the human DPP4 gene sequence encoding the extracellular domain of the human DPP4 protein. In one embodiment, the human DPP4 gene sequence replacing the rodent Dpp4 gene sequence comprises all 24 exons of the human DPP4 gene sequence encoding the extracellular domain of the human DPP4 protein. In one embodiment, the rodent is a mouse. In one embodiment, the rodent is a rat.

In one embodiment, the human or humanized DPP4 gene sequence replacing the rodent Dpp4 gene sequence encodes an extracellular domain of the DPP4 protein that is about 85%, 90%, 95%, 96%, 97%, 98%, or about 99% identical to the extracellular domain of a human DPP4 protein.

In one embodiment, the replacement is at an endogenous rodent Dpp4 locus and the human DPP4 gene sequence comprising one or more exons of the human DPP4 gene sequence encoding human or humanized DPP4 protein is operably linked to endogenous rodent regulatory elements or sequences at the endogenous rodent Dpp4 locus.

In one aspect, a method is provided for making a humanized DPP4 mouse, comprising replacing a mouse Dpp4 gene sequence encoding mouse Dpp4 protein with a human DPP4 gene sequence encoding human or humanized DPP4 protein.

In one embodiment, the replacement is at an endogenous mouse Dpp4 locus, and the human DPP4 gene encoding human or humanized DPP4 protein is operably linked to mouse regulatory elements or sequences at the endogenous mouse Dpp4 locus.

In one embodiment, the replacement is at an endogenous mouse Dpp4 locus, and the human DPP4 gene encoding human or humanized DPP4 protein is operably linked to endogenous mouse regulatory elements or sequences at the endogenous mouse Dpp4 locus.

In various aspects, the genetically modified non-human animals, e.g., rodents, e.g., mice or rats, described herein comprise the genetic modifications in their germ-line.

In one aspect, a non-human animal, e.g., rodent, e.g., a mouse or rat, embryo comprising a genetic modification as described herein is provided.

In one aspect, a non-human animal, e.g., rodent, e.g. a mouse or rat, host embryo is provided that comprises a donor cell that comprises a genetic modification as described herein.

In one aspect, a pluripotent or totipotent non-human animal, e.g., rodent, e.g., mouse or rat, cell comprising a genetic modification as described herein is provided. In one embodiment, the cell is a rodent cell. In one embodiment, the cell is a mouse cell. In one embodiment, the cell is a rodent embryonic stem (ES) cell. In one embodiment, the cell is a mouse ES cell.

In one aspect, a non-human animal, e.g., rodent, e.g., mouse or rat, egg is provided, wherein the non-human animal egg comprises an ectopic non-human animal chromosome, wherein the ectopic non-human animal chromosome comprises a genetic modification as described herein. In one embodiment, the non-human animal is a rodent. In one embodiment, the rodent is a mouse. In one embodiment, the rodent is a rat.

In one aspect, the mouse embryo, egg, or cell that is genetically modified to comprise a human DPP4 gene is of a mouse that is of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/01a. In another embodiment, the mouse is a 129 strain selected from the group consisting of a strain that is 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain. In one embodiment, the mouse is Swiss or Swiss Webster mouse.

In various aspects, the non-human animals comprising a human or humanized DPP4 nucleic acid sequence are selected from mammals and birds. In one embodiment, the non-human animals are mammals. In one embodiment, the mammals are rodents. In one embodiment, the rodents are mice or rats.

In one aspect, a rodent is provided that comprises a nucleic acid sequence comprising a human DPP4 gene or fragment thereof, where the human DPP4 gene or fragment thereof comprises at least one exon of the human DPP4 gene, and where the human DPP4 gene or fragment thereof encodes a human or humanized DPP4 protein.

In one embodiment, the human DPP4 gene or fragment thereof comprises at least 2, 3, 4, 5, 6, 7, 8, 9, 10, 11, 12, 13, 14, 15, 16, 17, 18, 18, 20, 21, 22, 23, 24, or 25 exons of the human DPP4 gene.

In one embodiment, the human DPP4 gene or fragment thereof comprises all 26 exons of the human DPP4 gene.

In one embodiment, the nucleic acid sequence further comprises a 5' flanking region of the human DPP4 gene. In one embodiment, the human DPP4 gene or fragment thereof is operably linked to the 5' flanking region of the human DPP4 gene. In one embodiment, the 5' flanking region of the human DPP4 gene comprises at least 1 kb in length (e.g., at least 1, 2, 3, 4, 5, 10, 20, 30, 40, 50 kb, or greater, in length). In one embodiment, the 5' flanking region of the human DPP4 gene comprises at least 10 kb in length. In one embodiment, the 5' flanking region of the human DPP4 gene comprises at least 40 kb in length.

In one embodiment, expression of the human DPP4 gene or fragment thereof is under control of the 5' flanking region of the human DPP4 gene.

In one embodiment, the human or humanized DPP4 protein comprises the amino acid sequence of SEQ ID NO: 24 or a fragment thereof.

In one embodiment, the rodent expresses the human or humanized DPP4 protein on the surface of T cells in a level that is at least about 20% (e.g., at least about 20%, 30%, 40%, 50%, 60%, 70%, 80%, 90%, 95%, 98%, 99%, or greater) of the level of rodent Dpp4 protein present on the surface of T cells of an age-matched rodent that expresses functional endogenous rodent Dpp4 protein but that does not comprise the human DPP4 gene or fragment thereof.

In one embodiment, the rodent expresses the human or humanized DPP4 protein on the surface of cells in one or more tissues selected from the group consisting of placenta, kidney, lung, liver, skeletal muscle, heart, brain, and pancreas, in a level that is at least about 20% (e.g., at least about 20%, 30%, 40%, 50%, 60%, 70%, 80%, 90%, 95%, 98%, 99%, or greater) of the level of rodent Dpp4 protein present on the surface of one or more tissues of an age-matched rodent that expresses functional endogenous rodent Dpp4 protein but that does not comprise the human DPP4 gene or fragment thereof.

In one embodiment, the rodent expresses functional endogenous rodent Dpp4 protein.

In one embodiment, the rodent is a mouse or a rat.

In one aspect, provided herein is a method for making a humanized transgenic rodent, comprising integrating a nucleic acid sequence comprising one or more exons of a human DPP4 gene sequence into a chromosome of a rodent, where the one or more exons of the human DPP4 gene sequence encodes a human or humanized DPP4 protein.

In one embodiment, the human DPP4 gene or fragment thereof comprises at least 2, 3, 4, 5, 6, 7, 8, 9, 10, 11, 12, 13, 14, 15, 16, 17, 18, 18, 20, 21, 22, 23, 24, or 25 exons of the human DPP4 gene.

In one embodiment, the human DPP4 gene or fragment thereof comprises all 26 exons of the human DPP4 gene.

In one embodiment, the nucleic acid sequence further comprises a 5' flanking region of the human DPP4 gene.

In one embodiment, the human DPP4 gene sequence is operably linked to the 5' flanking region of the human DPP4 gene.

In one embodiment, the human or humanized DPP4 protein comprises the amino acid sequence of SEQ ID NO: 24 or a fragment thereof.

In one embodiment, the rodent is a mouse or a rat. In further aspects, methods for determining the in vivo therapeutic efficacy of a human-specific DPP4 antagonist in any of the humanized DPP4 rodents described herein are provided, the method comprising administering to the rodent a DPP4 antagonist, wherein the rodent is infected with Middle East respiratory syndrome coronavirus (MERS-CoV); and determining if whether the DPP4 antagonist treats or prevents one or more symptoms of MERS-CoV infection compared to control rodents infected with MERS-CoV who have not been administered the DPP4 antagonist.

In one embodiment, the DPP4 antagonist is selected from the group consisting of small molecules, peptides and antibodies.

In one embodiment, the DPP4 antagonist is an antibody to a MERS-CoV protein.

In one embodiment, the MERS-CoV protein is MERS-CoV spike protein.

In one embodiment, the rodent is infected with one or more strains of MERS-CoV selected from the group consisting of Al-Hasa_1, Al-Hasa_2, Al-Hasa_3, Al-Hasa_4, Al-Hasa_12, Al-Hasa_15, Al-Hasa_16, Al-Hasa_17, Al-Hasa_18, Al-Hasa_19, Al-Hasa_21, Al-Hasa_25, Buraidah_1, EMC/2012, FRA/UAE, Hafr-Al-Batin_1, Hafr-Al-Batin_2, Hafr-Al-Batin_6, Jeddah_1, Jordan-N3/2012, Munich, Riyadh_3, Riyadh_4, Riyadh_5, Riyadh_14, Taif 1, Wadi-Ad-Dawasir_1, Riyadh_9, KFU-HKU 1, KFU-HKU 13, Qatar3, Qatar4, England 1, England-Qatar/2012, Bisha_1, Riyadh_1, and Riyadh_2.

In one embodiment, the antagonist is administered before MERS-CoV infection. In one embodiment, the antagonist is administered after MERS-CoV infection.

In one embodiment, the antagonist is administered simultaneously with MERS-CoV infection.

In one embodiment, the symptom of MERS-CoV infection is viral titer or RNA level.

In one embodiment, the viral titer or RNA level is assessed by one or more methods selected from the group consisting of qPCR, Northern Blot, plaque assay, and in situ hybridization, In one embodiment, the symptom of MERS-CoV infection is lung inflammation.

In one embodiment, the lung inflammation is assessed histochemically

In one embodiment, the symptom of MERS-CoV infection is weight loss.

In one embodiment, the rodent is a mouse or a rat. In one embodiment, the rodent is a mouse. In one embodiment, the rodent is a rat.

Each of the aspects and embodiments described herein are capable of being used together, unless excluded either explicitly or clearly from the context of the embodiment or aspect.

BRIEF DESCRIPTION OF THE DRAWINGS

FIG. 1A is a schematic showing that 78.8 kb of the mouse Dpp4 gene (top) spanning exon 2 through the stop codon in exon 26 are deleted and replaced with 81.7 kb of the human DPP4 gene (bottom) spanning exon 2 through exon 26 and a portion of the 3' untranslated region, as indicated. FIG. 1B is a schematic showing that the humanized DPP4 mouse comprises (i) the mouse Dpp4 gene 5' flanking region, including the regulatory sequences, e.g., promoter and transcription start site, and exon 1, including the initiation ATG codon, (ii) the human DPP4 gene spanning exon 2 through exon 26, including the Stop codon, and a portion of the 3'untranslated region, including the loxP site, and (iii) the mouse Dpp4 gene 3' untranslated region starting from just 3' to the Stop codon, as indicated.

FIG. 2 shows the amino acid sequence (SEQ ID NO:17) of the humanized DPP4 protein expressed in the humanized DPP4 mice.

FIG. 4 shows the H&E staining of airway (10× and 40× magnification) and alveoli (40× magnification) from the lungs of either mock (PBS)-infected, or MERS-CoV (Jordan strain)-infected, F0 humanized DPP4 mice 4 days after infection.

FIG. 5 is a sequence alignment of the mouse Dpp4 (mDpp4) amino acid sequence (SEQ ID NO: 25) with the human DPP4 (hDPP4) protein encoded by the transgenic MAID 7326/7327 mice (SEQ ID NO: 26). Non-homologous residues that differ between the sequences are underlined, homologous residues that differ between the sequences are bolded and italicized, and gaps are indicated by hyphens. Residues that are identical between the two sequences are shown in unformatted text.

FIG. 8 is a table displaying the primer-probe sets used for the human TaqManTm gain of allele assays, where 7333 hTU refers to the upstream set and 7333 hTD refers to the downstream set.

FIG. 9 is the amino acid sequence of the humanized DPP4 protein encoded by the transgenic MAID 7333 and 7334 mice (SEQ ID NO: 24).

FIG. 10A is a bar graph showing quantitative PCR measurements of MERS-CoV genome (UpE RNA) in infected mice 2 and 4 days post-infection (dpi). FIG. 10B is a bar graph showing quantitative PCR measurements of MERS-CoV mRNA transcript (leader RNA) in infected mice on 2 dpi and 4 dpi. FIG. 10C is a bar graph quantifying MERS-CoV viral titer of infected mouse lung at 2 dpi and 4 dpi. MERS-CoV levels in homogenized mouse lung were quantified by 50% Tissue Culture Infective Dose (TCID50) assay and expressed as plaque forming units (pfu) per mL. FIG. 10D is a panel of histological images, stained with Hematoxylin and Eosin, of lungs from MERS-CoV infected mice. Airway (10×), vasculature (10×) and interstitium (40×) are shown for PBS, 2 dpi, and 4 dpi mice.

Figure 17:
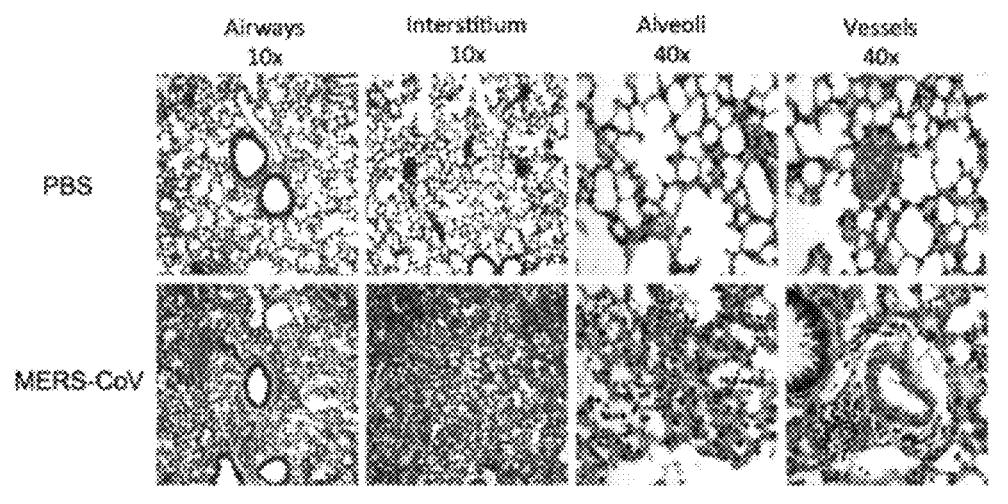

FIG. 17 depicts pathology (inflammation) as seen by histological examination at day 7 in a humanized DPP4 mouse exposed to a high dose of virus ($1\times10^6$ pfu/mouse) versus PBS-treated controls.

DETAILED DESCRIPTION

DPP4 Gene and Protein

Figure 1A:
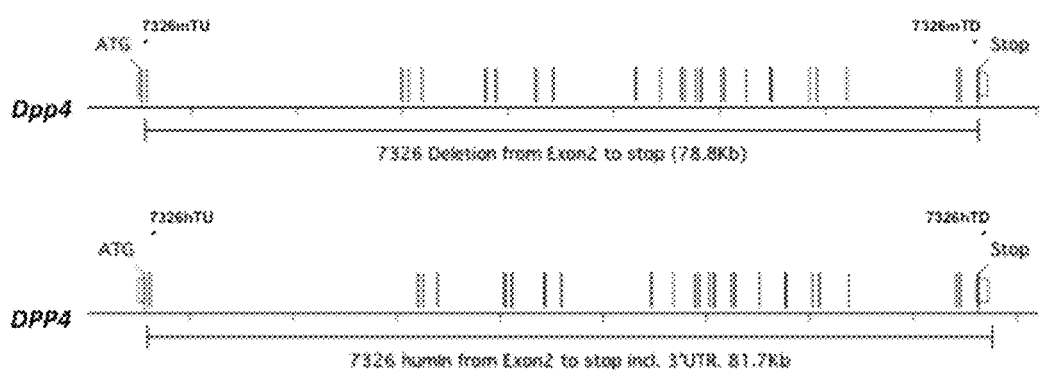
FIGS. 1A-B provide illustrations, not to scale, of the strategy for humanization of the Dpp4 locus.

The DPP4 gene encodes the type II transmembrane protein, tripeptidyl peptidase IV (DPP4) (also known as CD26, adenosine deaminase complexing protein-2 (ADCP2), adenosine deaminase binding protein (ADABP), and TP103), which has serine exopeptidase activity, and which plays an important role in the activation of T cells and in intracellular signal transduction cascades in several other cell types.

Human DPP4.

NCBI Gene ID: 1803; Primary source: HGNC:3009; RefSeq transcript: NM_001935.3; UniProt ID: P27487; Genomic assembly: GRCh38; Location: chr2:162,848,755-162,931,052 − strand. (See FIG. 6).

The human DPP4 gene is located on chromosome 2, at 2q24.3. The human DPP4 gene has 26 exons and encodes a type II transmembrane polypeptide of 766 amino acids in length, including an N-terminal 6 amino acid cytoplasmic domain, a 22 amino acid transmembrane domain, and a C-terminal 738 amino acid extracellular domain. The extracellular domain (i.e., ectodomain) of the human DPP4 protein is encoded by coding exons 3 through 26 of the human DPP4 gene.

Mouse Dpp44.

NCBI Gene ID: 13482; Primary source: MGI:94919; RefSeq transcript: NM_010074.3; UniProt ID: P28843; Genomic assembly: GRCm38; Location: chr2:62,330,073-62,412,591 − strand.

The mouse Dpp4 gene is located on chromosome 2, at 2 35.85 cM. The mouse Dpp4 gene has 26 exons and encodes a type II transmembrane polypeptide of 760 amino acids in length, including an N-terminal 6 amino acid cytoplasmic domain, a 22 amino acid transmembrane domain, and a C-terminal 732 amino acid extracellular domain. The extracellular domain (i.e., ectodomain) of the mouse Dpp4 protein is encoded by coding exons 3 through 26 of the mouse Dpp4 gene.

Species Specificity of DPP4 Protein

As discussed below in Example 2, the human, but not the mouse, DPP4 protein is a functional receptor for the Middle East respiratory syndrome coronavirus (MERS-CoV) infection.

Candidate therapeutic molecules that target the human DPP4 protein in a species-specific manner, or target molecules, such as MERS-CoV, which interact with the human DPP4 protein in a species-specific manner, are typically evaluated for pharmacokinetics (PK) and pharmacodynamics (PK) in non-human animals, e.g., rodents, e.g., mice or rats. Such therapeutic molecules are also tested for in vivo therapeutic efficacy in non-human animal, e.g., rodent, e.g., mouse or rat, models of human diseases, disorders and conditions in which DPP4 plays a role.

However, therapeutic molecules that are specific for the human DPP4 protein, e.g., human-specific DPP4 inhibitors, cannot be adequately evaluated for PD and/or in vivo therapeutic efficacy in rodents, in particular mice, because the targets of these therapeutic molecules are missing.

Moreover, therapeutic molecules that are specific for targets that specifically interact with human DPP4 protein, e.g., human DPP4-specific MERS-CoV, cannot be adequately evaluated for in vivo therapeutic efficacy in rodents, in particular mice, because the targets (e.g., receptor, interaction partner) of these therapeutic target molecules are missing.

Accordingly, in various embodiments, to assess the PD and/or in vivo therapeutic efficacy of a human-specific DPP4 protein antagonist or inhibitor in non-human animals, e.g., rodents, e.g., mice or rats, it is desirable to replace the endogenous Dpp4 protein with human or humanized DPP4 protein. In various embodiments, to assess the in vivo therapeutic efficacy of small molecules, peptides or biologic antagonists or inhibitors of a target molecule that specifically interacts with a human DPP4 protein in non-human animals, e.g., rodents, e.g., mice or rats, it is desirable to replace the endogenous Dpp4 protein with human or humanized DPP4 protein.

Further, in various embodiments, in order to avoid potential problems of the over- or under-expression of the human or humanized DPP4 protein, and/or the inappropriate expression of the human or humanized DPP4 protein in cells or tissues in which the endogenous Dpp4 protein is not normally expressed, it is desirable to insert the human DPP4 gene, in whole or in part, into the genome of the non-human animals, e.g., rodents, e.g., mice or rats, at the endogenous Dpp4 gene loci, and to express the human or humanized DPP4 protein in non-human animals, e.g., rodents, e.g., mice or rats, under the control, at least in part, of the endogenous Dpp4 regulatory elements.

In some embodiments, targeted replacement of the endogenous, e.g., mouse or rat, Dpp4 gene by the human DPP4 gene or fragment thereof is desirable.

In other embodiments, the human DPP4 gene or fragment thereof is randomly inserted into the rodent, e.g., mouse or rat, genome instead of replacing the endogenous Dpp4 gene with a human DPP4 gene or fragment thereof. In some embodiments, in rodents, e.g., mice or rats, in which the human DPP4 gene or fragment thereof has been randomly inserted into the genome, expression of endogenous rodent Dpp4 is retained.

Provided herein are non-human animals, e.g., rodents, e.g., mice or rats, that comprise a human DPP4 gene or fragment thereof either at (i.e., replacing) the endogenous Dpp4 locus, or at one or more other loci. Also provided herein are non-human animals, e.g., rodents, e.g., mice or rats, that comprise a human DPP4 gene or fragment thereof both at (i.e., replacing) the endogenous Dpp4 locus, and at an additional locus/loci.

In some embodiments, a fragment of a human DPP4 gene contains 200 kilobases (kb) or fewer nucleotides, e.g., 180, 160, 140, 120, 100, 80, 70, 60, 50, 40, 30, 20, 10, 5, 2.5, 1 kb or fewer nucleotides, e.g., 1000, 800, 600, 400, 200, or fewer nucleotides.

Generation of Cells and Non-Human Animals with Human DPP4

For targeted replacement of an endogenous non-human Dpp4 gene or fragment with a human DPP4 gene or fragment, a targeting construct is generated. See, e.g., Valenzuela et al. Nature Biotech, 21.6(2003):652-659; U.S. Pat. No. 6,586,251; and U.S. Pat. No. 8,759,105. For example, a targeting construct comprises homology arms flanking a replacement human DPP4 gene or fragment thereof.

In some embodiments, the replacement human DPP4 gene or fragment thereof comprises the entire human DPP4 gene. In other embodiments, the replacement human DPP4 gene or fragment thereof comprises a portion of the human DPP4 gene. For example, the replacement human DPP4 gene or fragment thereof comprises one or more exons of human DPP4 gene, e.g., 1, 2, 3, 4, 5, 6, 7, 8, 9, 10, 11, 12, 13, 14, 15, 16, 17, 18, 19, 20, 21, 22, 23, 24, 25, or 26 exons of the human DPP4 gene. For example, the replacement human DPP4 gene or fragment thereof comprises the exons 1-26 of the human DPP4 gene. In other embodiments, the replacement human DPP4 gene or fragment thereof comprises exons 2-26 of the human DPP4 gene. For example, the replacement human DPP4 gene or fragment thereof comprises intron 1 upstream of exon 2 through exon 26 of the human DPP4 gene. In some embodiments, the replacement human DPP4 gene or fragment thereof further comprises a human regulatory element(s), e.g., a portion of the human 3' untranslated region (UTR) downstream of the human DPP4 gene, for example at least 1 kb of downstream region (e.g., at least 1, 2, 3, 4, 5, 10, 20, 30, 40 Kb, or greater), and/or a human promoter or enhancer region upstream of the human DPP4 gene, for example, at least 10 kb of upstream region (e.g., at least 10, 20, 30, 40, 50 Kb, or greater).

Homology arms are sequences that are homologous to endogenous chromosomal nucleic acid sequences flanking the desired genetic modification/replacement, e.g., flanking the endogenous Dpp4 gene or fragment that is to be replaced. Homologous nucleic acid sequences can be two or more nucleic acid sequences that are either identical or similar enough that they are able to hybridize to each other or undergo intermolecular exchange. Due to the homology between the homology arms and the corresponding endogenous sequence, the homology arms direct the targeting construct to a specific chromosomal location within the genome, e.g., the endogenous Dpp4 gene locus. See, e.g., Valenzuela et al. Nature Biotech, 21.6(2003):652-659; U.S. Pat. No. 6,586,251; and U.S. Pat. No. 8,759,105.

Optionally, the targeting construct further comprises a selection marker, e.g., in between the two homology arms. Exemplary selection markers include antibiotic resistance markers (e.g., neomycin or kanamycin) and fluorescent proteins. In some embodiments, the selection marker is floxed, i.e., flanked by two loxP sites. The floxed selection marker can be removed by the addition of Cre recombinase, which catalyzes the excision of the floxed segment, e.g., including the selection marker.

Vector/Constructs

The transgenic non-human animals (e.g., rodents, e.g., mice or rats) of the invention can be made by using various vectors and/or constructs. In some embodiments, the targeting construct is in the form of a circular piece of double-stranded DNA, e.g., a bacterial artificial chromosome (BAC), plasmid, or P1-derived artificial chromosome (PAC).

To generate a non-human cell comprising a targeted replacement of the endogenous Dpp4 locus, a targeting construct containing a human DPP4 gene or fragment described herein is introduced into a non-human (e.g., rodent, e.g., mouse or rat) cell, e.g., embryonic stem (ES) cell.

To generate a non-human cell comprising a human DPP4 gene or fragment randomly inserted into the genome, a circular DNA construct, e.g., BAC, containing a human DPP4 gene or fragment thereof, is introduced into a non-human (e.g., rodent, e.g., mouse or rat) cell, e.g., ES cell. In some cases, the circular DNA construct, e.g., BAC, further contains a human DPP4 regulatory element, e.g., a human promoter or enhancer region upstream and/or downstream of human DPP4 gene. For example, the circular DNA construct contains at least 10 kb (e.g., at least 10, 20, 30, 40, 50 kb or greater) of promoter/enhancer region upstream of the ATG start codon of the human DPP4 gene. In addition or alternatively, the circular DNA construct contains at least 1 kb (e.g., at least 1, 2, 3, 4, 5, 10, 20, 30, 40 kb or greater) of untranslated region downstream of the human DPP4 gene. For example, the human DPP4 gene or fragment is operably linked to the human DPP4 regulatory element.

In some embodiments, the human DPP4 gene or fragment thereof in the circular DNA construct (e.g., BAC) comprises the entire human DPP4 gene. In other embodiments, the human DPP4 gene or fragment thereof comprises a portion of the human DPP4 gene. For example, the human DPP4 gene or fragment thereof comprises one or more exons of human DPP4 gene, e.g., 1, 2, 3, 4, 5, 6, 7, 8, 9, 10, 11, 12, 13, 14, 15, 16, 17, 18, 19, 20, 21, 22, 23, 24, 25, or 26 exons of the human DPP4 gene. For example, the human DPP4 gene or fragment thereof comprises the exons 1-26 of the human DPP4 gene. In other embodiments, the human DPP4 gene or fragment thereof comprises exons 2-26 of the human DPP4 gene. For example, the human DPP4 gene or fragment thereof comprises intron 1 upstream of exon 2 through exon 26 of the human DPP4 gene.

For example, the introduction step into the cell is done by electroporation or lipid-mediated transfection.

Optionally, the circular DNA construct, e.g., BAC, is linearized before introduction into the cell. For example, linearization is performed with rare-cutting restriction enzymes, e.g., SgrDI, SfiI, NotI, PacI, or SwaI.

In cases in which the targeting construct comprises an antibiotic selection marker (e.g., neomycin), cells that have taken up the targeting construct are optionally selected in neomycin/G418-containing media. Cells that survive and/or proliferate in neomycin/G418-containing media are selected and positive for the targeting construct.

In some embodiments, the cell population is screened for those cells that have incorporated into their genome a human DPP4 gene or fragment thereof, e.g., randomly inserted into the genome or targeted (e.g., by the targeting construct) to the endogenous Dpp4 locus.

Methods for screening include quantitative PCR and fluorescence in situ hybridization. See, e.g., U.S. Pat. No. 6,586,251 B2 and U.S. Pat. No. 8,759,105 B2. For example, methods of screening include detecting for the presence of a human DPP4 gene or fragment. In some embodiments, methods of screening include detecting for a loss of copy number of endogenous Dpp4 gene or fragment and/or gain of copy number of human DPP4 gene or fragment. Exemplary methods of screening are described in Examples 1 and 3.

In some embodiments in which the targeting construct comprises a floxed selection marker, correctly targeted cells are optionally further electroporated with a Cre-expressing vector, e.g., transiently expressing Cre recombinase, to remove the floxed selection marker.

To generate transgenic animals, positive ES cell clones, e.g., without floxed selection marker, containing a human DPP4 gene or fragment thereof, are introduced into a rodent embryo, e.g., a mouse or rat embryo, such as an 8-cell stage mouse embryo. For example, the introduction step is done by blastocyst injection technology, aggregation techniques, nuclear transfer and cloning, and/or the VelociMouse® method. See, e.g., U.S. Pat. No. 8,759,105 B2, U.S. Pat. No. 7,294,754, U.S. Pat. No. 7,576,259, and U.S. Pat. No. 7,659,442. For example, an ES cell clone is a subpopulation of cells derived from a single cell of the ES cell population following introduction of DNA and subsequent selection.

In some cases, DNA from transgenic non-human animals are screened in similar ways as described above to confirm transmittance of the human DPP4 gene/fragment through the germline.

In some embodiments, the humanized DPP4 rodents described herein are heterozygous for the human DPP4 allele. As such, these rodents have one human DPP4 allele and one wild-type rodent DPP4 allele. In other embodiments, the humanized DPP4 rodents are homozygous for the human DPP4 allele.

Uses for Humanized DPP4 Rodents

Humanized DPP4 rodents, e.g., mice or rats, are useful to evaluate the pharmacodynamics (PD) of human-specific DPP4 antagonists, e.g., small molecule, peptide or biologic inhibitors, useful for the treatment of hyperglycemia.

Pharmacokinetics (PK) and PD assays in humanized DPP4 rodents, e.g, mice or rats, are performed according to standard procedures known in the art.

Humanized DPP4 rodents, e.g., mice or rats, are useful to evaluate the in vivo therapeutic efficacy of human-specific DPP4 antagonists, e.g., small molecule, peptide or biologic inhibitors, in the treatment of hyperglycemia.

Humanized DPP4 rodents, e.g., mice or rats, are useful to test the in vivo therapeutic efficacy of antagonists, e.g., small molecule, peptide or biologic inhibitors, e.g., neutralizing antibodies, that are specific for target molecules, e.g., MERS-CoV (e.g., spike protein (S) of MERS-CoV, e.g., receptor binding domain of the spike protein of MERS-CoV), which specifically interact with human DPP4, in the treatment or prevention (or prophylaxis) of MERS-CoV infection. In some embodiments, rodents that are heterozygous for the human DPP4 allele are used to test the in vivo therapeutic efficacy of one or more antagonists in the treatment or prevention (or prophylaxis) of MERS-CoV infection. In other embodiments, DPP4 rodents that are homozygous for the human DPP4 allele are used to test the in vivo therapeutic efficacy of one or more antagonists in the treatment or prevention (or prophylaxis) of MERS-CoV infection.

Exemplary MERS-CoV strains include MERS-CoV Jordan strain (GenBank accession no. KC776174.1, MERS-CoV-Hu/Jordan-N3/2012) and MERS-CoV EMC/2012 strain (GenBank accession no. JX869059.2). In some embodiments, a MERS-CoV virus described herein comprises a MERS-CoV clinical isolate. In other embodiments, a MERS-CoV virus described herein comprises a strain comprising the same spike protein receptor binding domain (RBD) sequence as a clinical isolate described herein. Exemplary clinical isolates are shown in the table below. The table shows the amino acid sequence variation within the receptor binding domain (RBD) of the spike protein of several MERS-CoV clinical isolates. National Center for Biotechnology Information (NCBI)-deposited sequences of MERS-CoV clinical isolates were aligned at amino acids 367-606 and compared to that of the EMC/2012 strain. Clinical isolates harboring the A431P, S457G, S460F, A482V, L506F, D509G, and V534A substitutions (where the amino acid (single letter designation) preceding the number is that of the EMC/2012 strain, and the amino acid (single letter designation) following the number is that of the clinical isolate) are shown in the table.

In some embodiments, an antagonist is administered before (e.g., at least 1, 2, 4, 6, 12, 24, 48 hours, 2, 3, 4, 5, 6, or 7 days, or more before) a MERS-CoV infection in the rodent. In other embodiments, the antagonist is administered after (e.g., at least 1, 2, 4, 6, 12, 24, 48 hours, 2, 3, 4, 5, 6, or 7 days, or more after) a MERS-CoV infection in the rodent.

In some embodiments, where an antagonist is administered to a rodent after MERS-CoV infection, a lower viral titer or RNA level (e.g., viral UpE or leader sequence RNA level) in the rodent after administration of the antagonist, e.g., lower by at least 5-fold (e.g., at least 5, 10, 50, 100, 500, 1000, $10^4$, $10^5$, $10^6$, $10^7$-fold or more) compared to a control level indicates that the antagonist is effective in treating a MERS-CoV infection. For example, a control level is the viral titer or RNA level in the rodent prior to administration of the antagonist. In other examples, a control level is the viral titer or RNA level in a virus-infected rodent that is untreated with the antagonist.

In some embodiments, where an antagonist is administered to a rodent prior to MERS-CoV infection, a lower viral titer or RNA level (e.g., viral UpE or leader sequence RNA level) in the rodent after administration of the antagonist, e.g., lower by at least 5-fold (e.g., at least 5, 10, 50, 100, 500, 1000, $10^4$, $10^5$, $10^6$, $10^7$-fold or more) compared to a control level indicates that the antagonist is effective in preventing a MERS-CoV infection. For example, a control level is the viral titer or RNA level of a rodent infected with MERS-CoV that was not treated with the antagonist.

TABLE I

| No variation from EMC/2012 sequence | A431P | S457G | S460F | A482V | L506F | D509G | V534A |
|---|---|---|---|---|---|---|---|
| Al-Hasa_1 | Riyadh_9 | KFU-HKU 1 | Qatar3 | Riyadh_9 | England 1 | Bisha_1 | Riyadh_2 |
| Al-Hasa_2 | | KFU-HKU 13 | Qatar4 | | England-Qatar/2012 | Riyadh_1 | |
| Al-Hasa_3 | | | | | | | |
| Al-Hasa_4 | | | | | | | |
| Al-Hasa_12 | | | | | | | |
| Al-Hasa_15 | | | | | | | |
| Al-Hasa_16 | | | | | | | |
| Al-Hasa_17 | | | | | | | |
| Al-Hasa_18 | | | | | | | |
| Al-Hasa_19 | | | | | | | |
| Al-Hasa_21 | | | | | | | |
| Al-Hasa_25 | | | | | | | |
| Buraidah_1 | | | | | | | |
| EMC/2012 | | | | | | | |
| FRA/UAE | | | | | | | |
| Hafr-Al-Batin_1 | | | | | | | |
| Hafr-Al-Batin_2 | | | | | | | |
| Hafr-Al-Batin_6 | | | | | | | |
| Jeddah_1 | | | | | | | |
| Jordan-N3/2012 | | | | | | | |
| Munich | | | | | | | |
| Riyadh_3 | | | | | | | |
| Riyadh_4 | | | | | | | |
| Riyadh_5 | | | | | | | |
| Riyadh_14 | | | | | | | |
| Taif_1 | | | | | | | |
| Wadi-Ad-Dawasir_1 | | | | | | | |

In some embodiments, viral RNA levels in a rodent lung can be determined by extracting RNA from the rodent lung by homogenization in a solution containing phenol, e.g., a solution containing phenol and guanidinium isothiocyanate (e.g., Trizol® (Life Technologies, Inc)). For example, the lung can be homogenized using a Magnalyzer (Roche) according to the manufacturers' instructions. In some embodiments, levels of MERS-CoV RNA can be assessed using quantitative PCR (qPCR) using primers that target the MERS-CoV genome and/or primers that target the MERS-CoV mRNA transcript. For example, the Taqman® Fast virus one-step master mix (Applied Biosystems) can be used in qPCR according to the manufacturers' instructions using a duplex of primers obtained from Life Technologies targeting a region of the genome upstream of the envelope gene (UpE) or the leader sequence of the nucleocapsid messenger RNA (leader primer), and compared to an endogenous control, such as rodent (e.g., mouse) 18S rRNA. For example, qPCR reactions in Microamp® fast optical reaction plates (Applied Biosystems) can be read on a 7500 fast DX real-time PCR instrument (Applied Biosystems). In some examples, qPCR data can be analyzed using the delta Ct method, with an uninfected control set to 1. For example, percent MERS-CoV RNA detected can be expressed relative to levels of RNA detected in infected mice treated with control antagonist, e.g., isotype-matched control antibodies, in cases where the antagonist is an antibody against MERS-CoV.

In some embodiments, the viral titer in a rodent lung can be determined by homogenizing the rodent lung in a buffer (e.g., phosphate buffered saline (PBS)), centrifuged (e.g., at 10,000 rpm). The supernatant can be analyzed by plaque assay on mammalian cells, such as Vero cells (e.g., Vero E6 cells) to quantitate levels of virus remaining after treatment with an antagonist. A standard plaque assay can be used, e.g., a plaque assay described in Page et al. (2012) Induction of alternatively activated macrophages enhances pathogenesis during severe acute respiratory syndrome coronavirus infection, *J Virol* 86:13334-13349. In some examples, the Page et al. plaque assay can be modified by leaving plates for 3 days for plaques to appear.

In some embodiments, less inflammation (e.g., interstitial or peri-vascular inflammation), fewer inflammatory cells, and/or less bronchiolar cuffing, e.g., determined by histological analysis, in a lung sample of a rodent treated with an antagonist prior to or after MERS-CoV infection compared to a control lung sample can indicate that the antagonist is effective in treating or preventing a MERS-CoV infection. For example, a control lung sample can be from a rodent infected with MERS-CoV that is untreated with an antagonist, e.g., untreated before and/or after infection.

The rodents described herein are useful for the efficient testing of drugs and vaccines for MERS-CoV, e.g., to demonstrate safety and efficacy prior to clinical testing in humans. They permit rapid identification and/or validation of therapeutics/prophylactics, e.g., within several weeks of testing.

Definitions

Homologous amino acid residues are residues that share similar characteristics or properties. Characteristics or properties of an amino acid residue are based on, e.g., the structure of the polypeptide backbone, for example, a sheet or helical conformation, the charge or hydrophobicity of the residue, and/or the bulk of the side chain(s). For example, homologous residues are similar in side chain properties, e.g., polarity, charge, size, aromaticity, and/or hydrophobicity.

The term, "about" refers to a stated value plus or minus another amount; thereby establishing a range of values. In certain embodiments, "about" indicates a range relative to a base (or core or reference) value or amount plus or minus up to 15%, 14%, 13%, 12%, 11%, 10%, 9%, 8%, 7%, 6%, 5%, 4%, 3%, 2%, 1%, 0.75%, 0.5%, 0.25% or 0.1%.

For example, about refers to a range of +/−5% below and above the recited numbers, e.g., numbers of nucleotide bases.

The term "operably linked" as used herein refers to positions of components so described, e.g., nucleotide sequences, are in a relationship permitting them to function in their intended manner.

As used herein, the term "protein" includes polypeptides, peptides, fragments of polypeptides, and fusion polypeptides.

As used herein, a "nucleic acid" refers to two or more deoxyribonucleotides and/or ribonucleotides covalently joined together in either single or double-stranded form.

The term "replacement" in reference to gene replacement refers to placing exogenous genetic material at an endogenous genetic locus, thereby replacing all or a portion of the endogenous gene with an orthologous or homologous nucleic acid sequence. In one instance, an endogenous non-human gene or fragment thereof is replaced with a corresponding human gene or fragment thereof. A corresponding human gene or fragment thereof is a human gene or fragment that is an ortholog of, a homolog of, or is substantially identical or the same in structure and/or function, as the endogenous non-human gene or fragment thereof that is replaced.

As used herein, the term "rodent" refers to any member of the order Rodentia. Examples of rodents include, without limitation, mice, rats, squirrels, prairie clogs, porcupines, beavers, guinea pigs, and hamsters. In one embodiment, a rodent is a rat. In another embodiment, a rodent is a mouse.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The following examples are provided for illustrative purposes only and not intended to limit the invention in any manner.

EXAMPLES

Example 1

Replacement of the Endogenous Mouse Dpp4 Gene with a Human DPP4 Gene

The 81.8 kb human DPP4 gene containing exon 2 through exon 26 and a portion of the 3' untranslated region of the human DPP4 gene replaced 78.8 kb of the murine Dpp4 gene locus spanning exon 2 through the stop codon in exon 26. See FIGS. 1A and 1B.

A targeting construct for replacing the mouse with the human DPP4 gene in a single targeting step was constructed using VelociGene® genetic engineering technology (see Valenzuela et al. (2003) High-throughput engineering of the mouse genome coupled with high-resolution expression analysis, Nature Biotech, 21(6):652-659). Mouse and human DPP4 DNA were obtained from bacterial artificial chromosome (BAC) clones RP23-362N15 and RP11-68L22, respectively. Briefly, an SgrDI linearized targeting construct generated by gap repair cloning containing mouse Dpp4 upstream and downstream homology arms flanking 82 kb of human DPP4 sequence extending from intron 1 upstream of exon 2 through exon 26, including the stop codon and a portion of the 3' untranslated region (genomic coordinates of the entire human DPP4 gene: GRCh38: chr2:162,848,755-162,931,052 (– strand)), and a floxed neo selection cassette, was electroporated into VGB6 mouse embryonic stem (ES) cells (derived from C57BL/6N mice). Correctly targeted ES cells (MAID 7326) were further electroporated with a transient Cre-expressing vector to remove the drug selection cassette. Targeted ES cell clones without drug cassette (MAID 7327) were introduced into an 8-cell stage SW mouse embryo by the VelociMouse® method (see, U.S. Pat. Nos. 7,294,754, 7,576,259, 7,659,442, and Poueymirou et al. (2007) F0 generation mice that are essentially fully derived from the donor gene-targeted ES cells allowing immediate phenotypic analyses Nature Biotech. 25(1):91-99). VelociMice® (F0 mice fully derived from the donor ES cell) bearing the humanized DPP4 gene were identified by genotyping for loss of mouse allele and gain of human allele using a modification of allele assay (see, Valenzuela et al. (2003)).

Correctly targeted ES cell clones were identified by a loss-of-native-allele (LONA) assay (Valenzuela et al. 2003) in which the number of copies of the native, unmodified Dpp4 gene were determined by two TaqMan™ quantitative polymerase chain reactions (qPCRs) specific for sequences in the mouse Dpp4 gene that were targeted for deletion. The qPCR assays comprised the following primer-probe sets (written 5' to 3'): upstream forward primer, TCGCCACTGT GCCTAACATA G (SEQ ID NO:1); upstream reverse primer, CCGGGACTAA ACTGGAACAT TC (SEQ ID NO:2); upstream probe, FAM-TCAGTCAACT TCT-TCTGGGT TGTTTCC-BHQ (SEQ ID NO:3); downstream forward primer, CAGCTCTGGT GGAGAACTAG AC (SEQ ID NO:4); downstream reverse primer, GGAGGTC-CTC GGTCTTTAGA AG (SEQ ID NO:5); downstream probe, FAM-TCACACTTAG GCTTATAAAC CATTC-CCGT-BHQ (SEQ ID NO:6); in which FAM refers to the 5-carboxyfluorescein fluorescent probe and BHQ refers to the fluorescence quencher of the black hole quencher type (Biosearch Technologies). DNA purified from ES cell clones that have taken up the targeting vector and incorporated in their genomes was combined with TaqMan™ Gene Expression Master Mix (Life Technologies) according to the manufacturer's suggestions in a 384-well PCR plate (Micro-Amp™ Optical 384-Well Reaction Plate, Life Technologies) and cycled in an Applied Biosystems Prism 7900HT, which collects fluorescence data during the course of the PCRs and determines a threshold cycle (Ct), the fractional PCR cycle at which the accumulated fluorescence reaches a pre-set threshold. The upstream and downstream DPP4-specific qPCRs and two qPCRs for non-targeted reference genes were run for each DNA sample. The differences in the Ct values (ΔCt) between each DPP4-specific qPCR and each reference gene qPCR were calculated, and then the difference between each ΔCt and the median ΔCt for all samples assayed was calculated to obtain ΔΔCt values for each sample. The copy number of the DPP4 gene in each sample was calculated from the following formula: copy number=$2 \times 2^{-\Delta \Delta Ct}$. A correctly targeted clone, having lost one of its native copies, will have a Dpp4 gene copy number equal to one. Confirmation that the human DPP4 gene sequence replaced the deleted mouse Dpp4 gene sequence in the humanized allele was confirmed by a TaqMan™ qPCR assay that comprises the following primer-probe sets (written 5' to 3'): human upstream forward primer, GCG-GTCTCCC TCTTCTAACG (SEQ ID N0:7); human upstream reverse primer, GCAAGCCGAG CAGATCAAG (SEQ ID NO:8); human upstream probe, FAM-ACTC-CCACCT GCAAATCCTG CTGC-BHQ (SEQ ID NO:9); human downstream forward primer, AACCGCACTG GCATATGGA (SEQ ID NO:10); human downstream reverse primer, TACAAGGTAG TCTGGGATTA CTAACAAAA (SEQ ID NO:11); human downstream probe, FAM-ACATTTATCT AGAAAGGCTC-BHQ (SEQ ID NO:12).

The same LONA assay is used to assay DNA purified from tail biopsies for mice derived from the targeted ES cells to determine their DPP4 genotypes and confirm that the humanized DPP4 allele is transmitted through the germline. Two pups heterozygous for the replacement are bred to generate a mouse that is homozygous for the replacement of the endogenous mouse Dpp4 gene by the human DPP4 gene. Pups that are homozygous for the replacement are used for phenotyping.

The upstream junction of the murine Dpp4 locus and the sequence containing the human DPP4 gene is designed to be within 5'-AGGAGAGAAG CCAACAAGAT CATAAGATCA TGCTCAGGGC CAAAATTCAA GGGCTTCTGC (CGTCGACG) GCCTTAGAGA ACTC-CAACTG GCGCACTCCA GACGCCACCC CCAC-CCCCAG CCCGCGGTCT CCCTCTTCTA ACG-CACTCCC ACCTGCAAAT (SEQ ID NO:13), wherein the human DPP4 sequences are italicized, and the SgrDI restriction site is bracketed. The downstream junction of the sequence containing the human DPP4 gene and the floxed neo selection cassette is designed to be within 5'-TTATTC-CAGG GAACTATGAT GAGGCTTATA TAAGAACGAA TAAGATCAGA AATATCATTC TGGCAGTTCT TATG-GCTCAG ctcgag(ataa cttcgtataa tgtatgctat acgaagttat) atg-catggcc tccgcgccgg gttttaggcgc ctcccgcggg (SEQ ID NO:14), wherein the human DPP4 sequences are italicized, the neo cassette sequences are in lower case, and the loxP site is bracketed. The downstream junction of the sequence of the floxed neo selection cassette and the murine Dpp4 locus is designed to be within 5'-atgtctgga(a taacttcgta taatgtatgc tatacgaagt tat)gctagta actataacgg tcctaaggta gcgagctagc CAGCATAGCT CTCCATAGCT TATT-TAAGAC CACATTTGTT CTCATTATCT CAAAAGT-GCA CTGTTAAGAT GAAGATCTTA (SEQ ID NO:15), wherein the neo cassette sequences are in lower case, and the loxP site is bracketed. After removal of the neo selection cassette, the junction of the sequence containing the human DPP4 gene, the loxP site remaining after removal of the neo selection cassette, and the murine Dpp4 locus is designed to be within 5'-TATTCCAGGG AACTATGATG AGGCT-TATAT AAGAACGAAT AAGATCAGAA ATATCATTCT GGCAGTTCTT ATGGCTCAG ctcgag(ataa cttcgtataa tgtat-gctat acgaagttat) gctagtaact ataacggtcc taaggtagcg agctagcCA GCATAGCTCT CCATAGCTTA TTTAAGACCA CATTTGTTCT CATTATCTCA AAAGT-
GCACT GTTAAGATGA AGATCTTAAT AATGTTCAT
TGAGACATTT CAGGCTGCTT TCTCCAGTTT TACAC-
CTGCA ATCCTAACTA AGGATGCCTG TCCCCAGAAC
(SEQ ID NO:16), wherein the human DPP4 sequences are italicized, the neo cassette sequences are in lower case, and the loxP site is bracketed.

FIG. 2 shows the amino acid sequence of DPP4 encoded by the humanized DPP4 nucleic sequence in MAID 7326/7327 (SEQ ID NO:17) is the same as human DPP4 because mouse Dpp4 codon 1, encodes only the first two amino acids of DPP4, Met and Lys, which are the same as those encoded by human DPP4 codon 1.

Example 2

Infection of Humanized DPP4 Mice by MERS-CoV

Middle East Respiratory Syndrome—Coronavirus (MERS-CoV) is a newly emergent virus that causes severe acute respiratory disease. The receptor for MERS-CoV is dipeptidyl peptidase IV (DPP4) (see Raj et al. (2013) Dipeptidyl Peptidase 4 is a Functional Receptor for the Emerging Human Coronavirus-EMC, Natuere 495(7440): 251-254). In vivo testing of anti-viral molecules requires an animal model, e.g., a small animal model, such as a rodent (e.g., mouse or rat), that is susceptible to MERS-CoV infection. However, recent studies have shown that mouse Dpp4 cannot support MERS-CoV infection (see, e.g., Cockrell et al. (2014) Mouse Dipeptidyl Peptidase is Not a Functional Receptor for Middle East Respiratory Syndrome Coronavirus (MERS-CoV) Infection, J. Virol. 88(9):5195-5199; and Coleman et al. (2014) Wild-Type and Innate Immune-Deficient Mice are Not Susceptible to the Middle East Respiratory Syndrome Coronavirus, J. Gen. Virol. 95(2):408-412), at least in part because the MERS-CoV Spike protein interacts with human, but not mouse, DPP4 (see, e.g., Coleman et al. (2013); and Raj et al. (2013)). Sequence comparison of the sequences of mouse and human DPP4 revealed that the amino acids that have previously been identified as contact sites between MERS-CoV spike (S) protein and its receptor differ between the two species. In addition, expression of human DPP4 in mouse cells allows for MERS-CoV virus entry and propagation, indicating that entry of the virus is the limiting step in infection of mouse cells, and that the lack of interaction between mouse DPP4 and the MERS-CoV glycoprotein defines the species tropism in vitro. See, e.g., Lu et al. (2013) Molecular basis of binding between novel human coronavirus MERS-CoV and its receptor CD26, Nature. 500 (7461):227-31; and Cockrell et al. (2014) Mouse Dipeptidyl Peptidase is Not a Functional Receptor for Middle East Respiratory Syndrome Coronavirus (MERS-CoV) Infection, J. Virol. 88(9):5195-5199.

As a consequence, normal mouse strains cannot be used to measure the efficacy of therapeutics targeting MERS-CoV. Zhao et al. (2014) Rapid Generation of a Mouse Model for Middle East Respiratory Syndrome, Proc. Natl. Acad. Sci. USA 111(13):4970-4975 have expressed human DPP4 in mice by adenovirus transduction, thereby allowing for MERS-CoV infection. However, this adenovirus model has several limitations, including: (a) the virus is cleared rapidly from infected mice; (b) there is a loss of human DPP4 expression over time; (c) the tissue distribution of virally-transduced DPP4 does not reflect expression seen in mice or humans; and (d) adenovirus infection induces an interferon response.

Figure 1B:
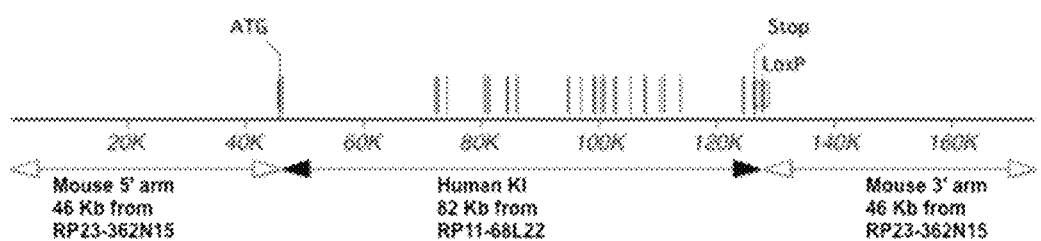

To generate a mouse model for MERS-CoV infection, humanized DPP4 mice were generated as described above in Example 1. As shown in FIG. 1B, exons 2 through 26 of mouse Dpp4 were replaced by the corresponding sequences of human DPP4. Because the remaining mouse Dpp4 coding exon 1 encodes only the first two amino acids of Dpp4, Met and Lys, which are the same as those in corresponding human DPP4 exon 1, the DPP4 protein expressed in humanized DPP4 mice is completely human (see FIG. 2, SEQ ID NO:17). Thus, humanized DPP4 mice express a fully human DPP4 under the control of the endogenous mouse regulatory sequences, i.e., 5' flanking region (promoter and enhancer(s)), and 3' untranslated region sequences. It is expected that the humanized DPP4 is expressed in the same cells and tissues, and at the same or similar levels, as mouse Dpp4 is expressed in wild-type mice lacking human DPP4 nucleic acid sequences.

Figure 3:
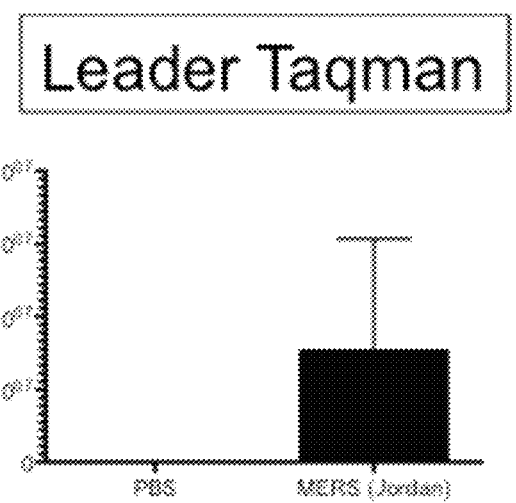
FIG. 3 shows the results of real-time PCR performed on RNA obtained from lung tissue from either mock (PBS)-infected, or MERS-CoV (Jordan strain)-infected, F0 humanized DPP4 mice 4 days after infection.
Figure 4:
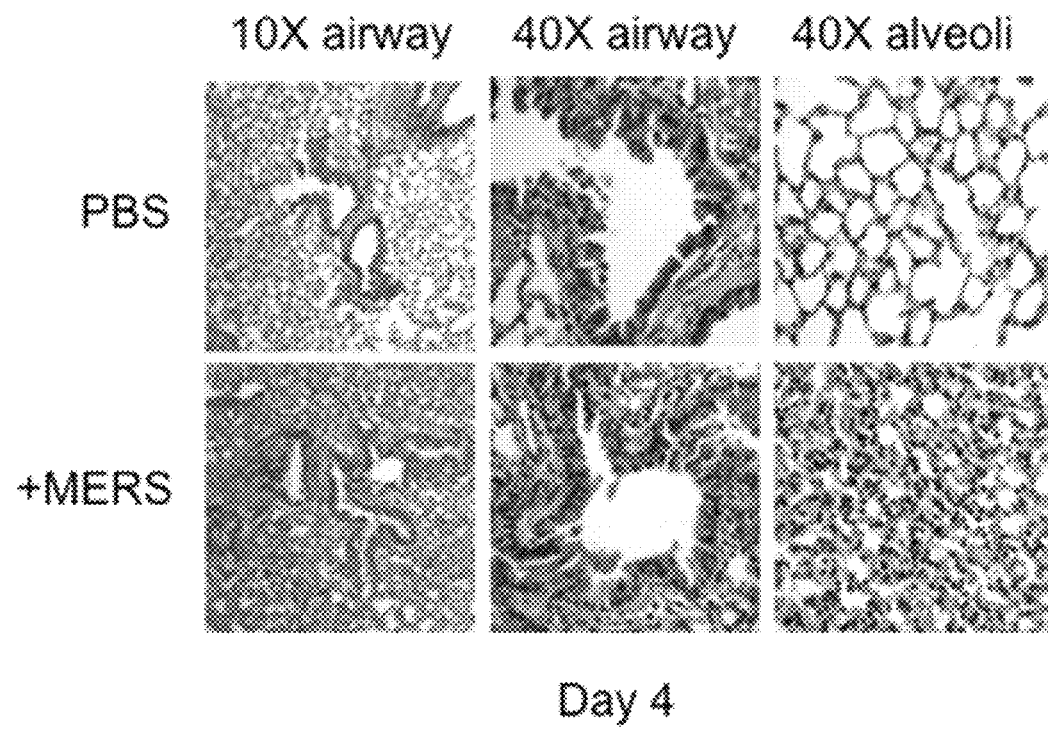

Two F0 humanized DPP4 mice were infected intranasally with MERS-CoV (Jordan strain) or mock treated with PBS. Four days post-infection, MERS-CoV RNA was quantified in the lungs by real-time PCR using primers specific for the replicative form of the MERS-CoV genome. Data was normalized to the amount of PCR product obtained from the lungs of the mock-infected mice (arbitrarily set at 1). FIG. 3 shows that MERS-CoV RNA could be amplified from lungs of the MERS-CoV-infected humanized DPP4 mice. H&E staining was also performed using lung tissue from mock- and MERS-CoV-infected mice. FIG. 4 shows that MERS-CoV infection of humanized DPP4 mice did not affect the airway, but resulted in thickening of the walls of the alveoli and less space between alveolar cells, indicating inflammation in the lungs associated with MERS-CoV infection.

In addition, 6 to 8 week old mice were inoculated intranasally with MERS-CoV, e.g., $2 \times 10^5$ pfu of MERS-CoV (Jordan). No mortality or clinical signs of disease were observed up to day 4 after inoculation. On days 2 and 4 post-inoculation, mice were euthanized and their lungs were dissected. To obtain virus RNA levels, lungs were homogenized in Trizol®, RNA extracted, and analyzed by real-time PCR using primers specific to MERS-CoV (FIGS. 10A and 10B). A set of primers was specific to a region of the viral genome upstream of the envelope gene (UpE), and another set of primers was specific to the leader sequence of the nucleocapsid mRNA (leader primer). Mouse 18S rRNA was used as endogenous control.

To obtain virus titers, lungs were homogenized in phosphate buffered saline (PBS), clarified by centrifugation, and titered on Vero E6 cells (FIG. 10C). For example, the supernatant was analyzed by a plaque assay on VeroE6 cells to quantitate the levels of virus present in the lungs. For example, plaque assays were performed as described in Page et al. (2012) Induction of alternatively activated macrophages enhances pathogenesis during severe acute respiratory syndrome coronavirus infection, *J Virol* 86:13334-13349, with plates left for 3 days for plaques to appear.

Robust MERS-CoV replication in the lungs was evident at 2 and 4 days post-infection. RNA quantification, using a primer set specific for MERS-CoV leader, which was designed to only amplify replicating MERS-CoV, demonstrated high levels of MERS-CoV replicating RNA in lungs collected at day 2, and these levels were maintained through day 4 post-infection (FIGS. 10A-B). Plaque assay of lung homogenate on Vero E6 cells quantified MERS-CoV (Jordan) levels of ~7.27×10$^4$ pfu/mL lung at day 2 and ~3.75× 10$^5$ pfu/mL lung at 4 days post-infection (FIG. 10C), demonstrating active replication of MERS-CoV in the lungs of the infected humanized DPP4 mice.

Also, lungs from humanized DPP4 mice intranasally inoculated with either MERS-CoV (Jordan strain) or PBS (mock infected) were analyzed for pathological changes (FIG. 10D). At day 2 post-infection, peri-bronchiolar inflammation was evident with alterations in bronchiolar cell structure found throughout the lungs. Minimal peri-vascular inflammation or effects on alveolar structures were observed at this time point. At 4 days post-infection, interstitial infiltration was observed with peri-vascular cuffing and extensive alveolar thickening. Bronchiolar alterations were present as well. See FIG. 10D. This pathology is consistent with the radiographic findings of development of interstitial pneumonia and significant lung disease seen in humans with MERS-CoV.

The above data shows that humanized DPP4 mice, such as those described herein, are susceptible to MERS-CoV infection. The data also demonstrate that the humanized DPP4 mice described herein are an in vivo model of MERS-CoV infection that recapitulates the pathology, e.g., pathological sequelae, that is seen in MERS-CoV infection of humans.

Thus, humanized DPP4 mice are a robust model of MERS-CoV that is useful to assess MERS-CoV treatment in vivo. For example, the humanized DPP4 mice are appropriate host animals to measure the pharmacokinetics, pharmacodynamics and therapeutic efficacy of therapeutic molecules that target MERS-CoV.

FIG. 5 shows a protein sequence alignment of mouse Dpp4 (SEQ ID NO: 25) and human DPP4 (encoded by the 7326/7327 transgenic mice) (SEQ ID NO: 26).

Next, a dose-response study of weight as a function of time post-infection of MERS-CoV was conducted in humanized DPP4 mice. Mice were infected with either MERS-CoV (Jordan strain) or PBS (mock infected) as described above and were analyzed for weight loss, which is a sign of productive infection, over a period of seven days. As shown in FIG. 14, humanized DPP4 mice exhibited productive infection (i.e., manifested disease pathology), with weight loss beginning 4 days post-infection. Four to five mice were used per group. FIG. 15 shows that mice that were heterozygotic for the humanized DPP4 allele were equally susceptible to infection by MERS-CoV, as they exhibited a similar degree of weight loss when compared to homozygotes. This finding is significant because it indicates that studies can be conducted using heterozygous mice. Additionally, use of heterozygous mice avoids any potential issue related to functional mouse Dpp4 knockouts that could potentially be present in homozygous humanized DPP4 mice.

Figure 16:
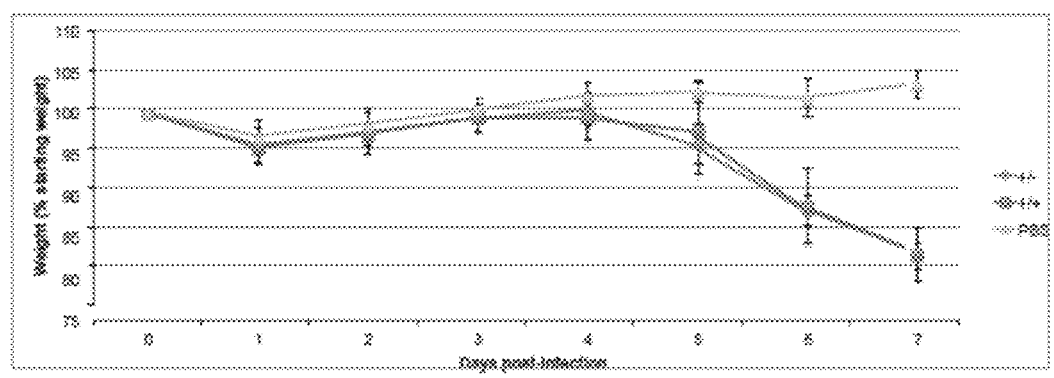
FIG. 16 depicts a dose-response study of weight as a function of time post-infection with MERS-CoV ($1\times10^6$ pfu/mouse; 4-5 mice per group) in heterozygotic and homozygotic humanized DPP4 mice.

The lungs of these mice were also examined histologically for inflammation according to the methods described above. As shown in FIG. 16, hDPP4 mice exposed to a high dose of virus (1×10exp6 pfu/mouse) exhibited increased pathology relative to PBS controls.

Example 3

Figures 6, 7:
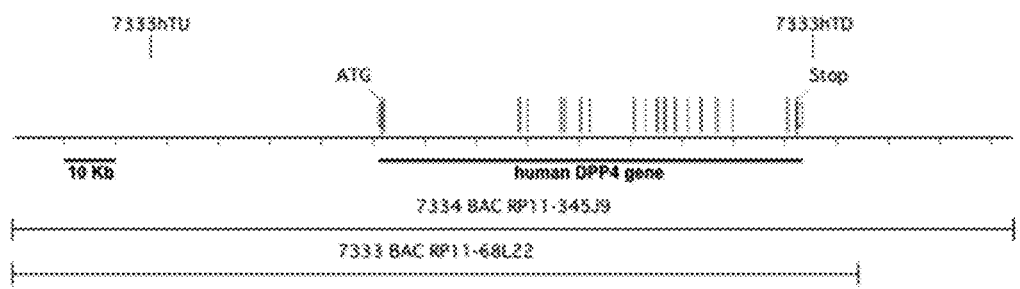
FIG. 6 is a table displaying gene, sequence, and chromosomal information for human DPP4.
FIG. 7 is a schematic showing the coverage of the human DPP4 gene and flanking genomic sequences for each of the BACs, BAC RP11-345J9 and BAC RP11-68L22. The locations within the human DPP4 gene and promoter regions at which the human TaqManTm primer-probe sets anneal are also shown (7333hTU for the upstream set and 7333hTD for the downstream set).

Generation of Transgenic Mice Containing the Human DPP4 Gene Using Random Insertion of BACs Transgenic mice were generated that contain the human DPP4 gene, for which the sequence and genomic information is shown in FIG. 6. Two different overlapping BACs containing the human DPP4 gene were used: BAC RP11-68L22 and BAC RP11-345J9 (FIG. 7). Both BACs contained the coding region of the human DPP4 gene, as well as over 40 kb of promoter region upstream of the ATG start codon of the DPP4 gene and several kilobases downstream of the stop codon of the DPP4 gene (FIG. 7).

To generate the BAC transgenic mice, each BAC DNA was electroporated into VGB6 mouse embryonic stem (ES) cells (derived from C57BL/6N mice). ES cells containing the coding region of the human DPP4 gene, as well as promoter regions of the gene, were introduced into an 8-cell stage SW mouse embryo by the SW mouse embryo by the VelociMouse® method (see, e.g., U.S. Pat. Nos. 7,294,754, 7,576,259, 7,659,442, and Poueymirou et al. (2007) F0 generation mice that are essentially fully derived from the donor gene-targeted ES cells allowing immediate phenotypic analyses Nature Biotech. 25(1):91-99).

Human gain of allele assays were used to screen ES cell clones for ones that contained copies of the human DPP4 gene along with promoter regions of the gene. Human gain of allele assays were also used to identify VelociMice® (F0 mice fully derived from the donor ES cell) bearing the humanized DPP4 gene along with promoter regions of the gene.

Briefly, genomic DNA was extracted from ES cell clones using standard methods and tested in a TaqManTm quantitative PCR (qPCR) assay using two sets of primer-probes to detect a human DNA sequence upstream (7333 hTU) and downstream (7333 hTD) of the human DPP4 coding sequence (FIG. 8). The locations within the human DPP4 gene and flanking regions (e.g., promoter regions) at which each primer-probe set annealed is shown in FIG. 7. A fluorescent read-out above background in the TaqManTm qPCR assay indicated the presence of the human DPP4 gene and at least 40 kb of the 5' flanking region of the human DPP4 gene that had been integrated into the transgenic mouse genome.

The 7333 hTU primer-probe set (written 5' to 3') was: human upstream forward primer, TGGCTTATTCTCTAT-TCCTCACCTA (SEQ ID NO: 18); human upstream probe, FAM-TGCTTTCCCTCCTCCCTTCTGA-BHQ (SEQ ID NO: 19); human upstream reverse primer, GGCCTTAGC-CCAGAAACTG (SEQ ID NO: 20). The 7333 hTD primer-probe set (written 5' to 3') was: human downstream forward primer, TGCAGACTTGTCTTGACATTCATA (SEQ ID NO: 21); human downstream probe, CAL-AGCCTCTGCA-GACACAGGAATGGC-BHQ (SEQ ID NO: 22); and human downstream reverse primer, TCTGGGCACTGGT-GTACTC (SEQ ID NO: 23); in which FAM and CAL refer to the 5-carboxyfluorescein and CAL Orange fluorescent probes, respectively, and BHQ refers to the fluorescence quencher of the black hole quencher type (Biosearch Technologies).

For example, genomic DNA from ES cell clones was combined with TaqMan™ Gene Expression Master Mix (Life Technologies) according to the manufacturer's suggestions in a 384-well PCR plate (MicroAmp™ Optical 384-Well Reaction Plate, Life Technologies) and cycled in an Applied Biosystems Prism 7900HT, which collects fluorescence data during the course of the PCRs and determines a threshold cycle (Ct), the fractional PCR cycle at which the accumulated fluorescence reaches a pre-set threshold. The upstream and downstream DPP4-specific qPCRs and two qPCRs for non-DPP4 reference genes were run for each DNA sample. The differences in the Ct values (Ct) between each DPP4-specific qPCR and each reference gene qPCR were calculated, and then the difference between each Ct and the median ΔCt for all samples assayed was calculated to obtain ΔΔCt values for each sample. The copy number of the DPP4 gene in each sample was calculated from the following formula: copy number=2×2$^{-\Delta\Delta Ct}$. A clone containing at least one copy of the human DPP4 plus promoter regions integrated into the chromosome had a DPP4 gene copy number equal to or greater than one.

The same human gain of allele assay was used to assay DNA purified from tail biopsies for mice derived from the ES cells to confirm that the humanized DPP4 allele along with the human 5' flanking regions were transmitted through the germline.

Using the BAC insertion and screening methods described herein, two transgenic mice with DNA encoding human DPP4 were confirmed. BAC RP11-68L22 was used to generate ES cell clones and transgenic mice referred to as MAID 7333, and BAC RP11-345J9 was used to generate ES cell clones and transgenic mice referred to as MAID 7334.

The protein encoded by the humanized DPP4 nucleic acid sequence in the MAID 7333 and 7334 mice had the amino acid sequence shown in FIG. 9 (SEQ ID NO: 24), which is the same as human DPP4 (as encoded by the transcript, NM_001935.3).

Example 4

Treatment of Humanized DPP4 Mice that were Infected with the MERS-CoV Virus

Transgenic mice with the humanized DPP4 gene and flanking promoter regions were tested for their ability to be infected by MERS-CoV and to serve as a model for assessing therapeutic molecules for treating or preventing MERS-CoV.

Transgenic MAID 7333 mice (e.g., generated by the methods described in Example 3) were treated with 200 μg of antibodies directed against MERS-CoV spike protein or isotype controls by intraperitoneal injection (ip). One day after antibody injection, the mice were infected intranasally with MERS-CoV. Four days after infection, lungs of the mice were harvested, and viral RNA levels were measured using real-time PCR (RT-PCR). In particular, levels of the genomic RNA (UpE) or replicating RNA (leader) (specific for the replicative form of the MERS-CoV genome) of MERS-CoV were measured.

The RT-PCR data is shown in the table below.

| Antibody | UpE[1] | Leader[1] |
|---|---|---|
| Anti-MERS-CoV spike protein 1 (Ab 1) | 0.356839562 | 0.273565089 |
| Anti-MERS-CoV spike protein 2 (Ab 2) | 0.254493202 | 0.206006238 |
| Anti-MERS-CoV spike protein 3 (Ab 3) | 1.989548316 | 1.112094283 |
| (IgG1) isotype control | 104.0889287 | 101.2578723 |
| (IgG4) isotype control | 100 | 100 |

[1]Averages (% of isotype control)

Treatment of transgenic mice with the antibodies decreased viral RNA levels (both UpE and Leader) by about 50-fold to about 500-fold.

The data described herein show that transgenic mice generated by targeted integration methods (Example 1) and random BAC insertion methods (Example 3) with human DPP4 were susceptible to infection by MERS-CoV. In addition, anti-MERS-CoV antibodies blocked infection in transgenic mice in vivo. Thus, transgenic mice with human DPP4 (e.g., generated by the methods described herein) are useful for evaluating the efficacy of therapeutics (e.g., antibodies) that target the MERS-CoV virus.

Example 5

Figure 11A:
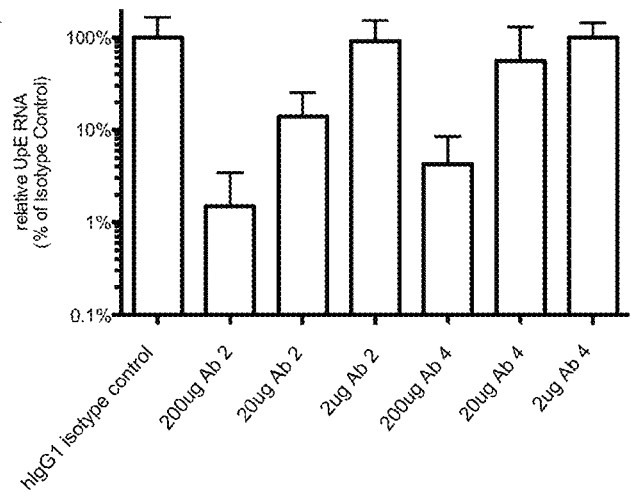
FIG. 11A is a bar graph showing quantitative PCR measurements of MERS-CoV genome (UpE RNA) from lungs of mice pre-treated with anti-MERS-CoV spike protein antibodies (Ab 2 or Ab 4) before viral infection.
Figure 11B:
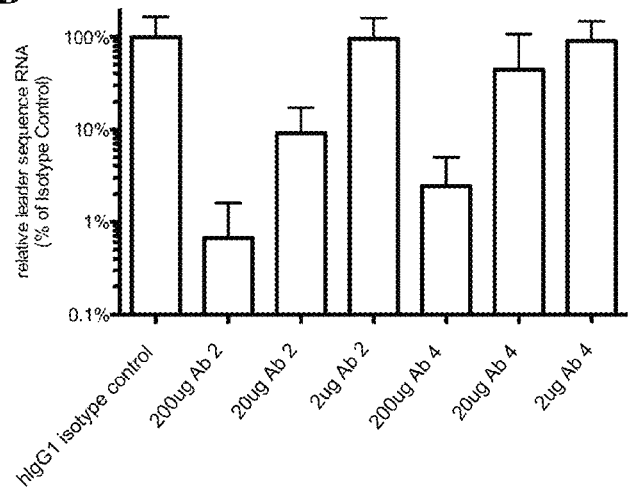
FIG. 11B is a bar graph showing quantitative PCR measurements of MERS-CoV mRNA transcript (leader RNA) from lungs of mice pre-treated with anti-MERS-CoV spike protein antibodies before viral infection. RNA was quantified using primers directed against the MERS-CoV genome and compared to hIgG1 isotype control treated mice. All samples were compared to hIgG1 control set at 100%.

Prophylactic Effects of Anti-MERS-CoV Antibodies on MERS-CoV Infection in Humanized DPP4 Mice The humanized DPP4 mice described herein were used to evaluate the prophylactic capability of the two monoclonal antibodies in vivo. Mice were i.p. injected with a dose range of anti-MERS-CoV antibodies-200 μg, 20 μg or 2 μg of anti-MERS-CoV spike protein antibody 2 (Ab 2), anti-MERS-CoV spike protein antibody 4 (Ab 4), or 200 μg of human IgG1 (hIgG1) isotype control antibody—at 24 hours before intranasal infection with 1×10$^5$ pfu of MERS-CoV (Jordan strain). Ab 2 and Ab 4 were fully human anti-MERS-CoV spike protein antibodies. RNA was extracted from the mouse lungs and analyzed by quantitative PCR as described above. For example, qPCR data was analyzed using the delta Ct method, with an uninfected control set to 1. Percent MERS-CoV RNA detected was expressed relative to levels of RNA detected in infected mice treated with isotype-matched control antibodies (FIGS. 11A-B). Also, viral titers from mouse lungs were determined as described above.

Figure 11C:
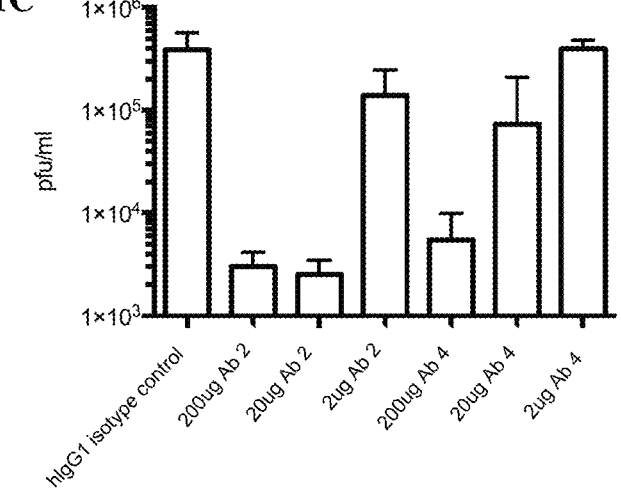
FIG. 11C is a bar graph showing the viral titer in lungs of mice pre-treated with anti-MERS-CoV spike protein antibodies before viral infection. Viral titer was quantitated by plaque assay and reported as pfu/mL.

Both antibodies significantly decreased MERS-CoV specific RNA levels in the lungs by over 2 logs at the 200 μg per mouse dose, compared to the isotype-matched control antibody (FIGS. 11A-B). Ab 2 was more effective at reducing MERS-CoV RNA levels at the 20 μg dose compared to Ab 4 at the same dose. The 2 μg dosing of either antibody was ineffective at reducing viral RNA levels compared to isotype control treated mice. When MERS-CoV titer was analyzed in the lungs (FIG. 11C), both the 200 μg and 20 μg dose of Ab 2 reduced virus levels to near the level of detection in the assay (2×10$^3$ pfu/ml). Ab 4 was equally efficient at the 200 μg dose as Ab 2, while the 20 μg and 2 μg doses displayed a dose dependent inhibition of viral inhibition. These data show that anti-MERS-CoV antibodies, e.g., Ab 2 and Ab 4, effectively blocked MERS-CoV infection in vivo.

Figure 12A:
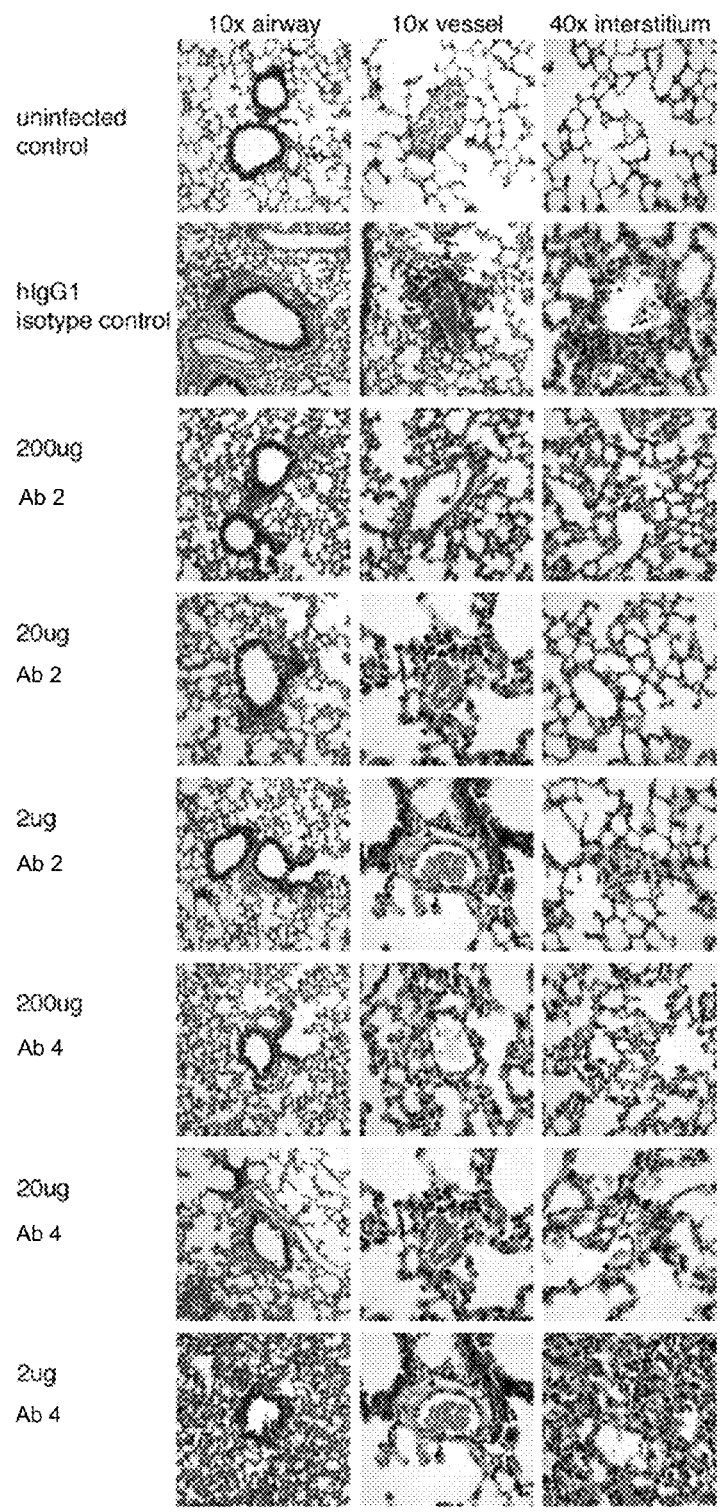
FIG. 12A is a panel of histological images of lungs of MERS-CoV infected B6/hDPP4 mice with anti-MERS-CoV spike protein antibody (Ab 2 or Ab 4) pre-treatment. Hematoxylin and Eosin stained sections of mouse lung showing airway, vasculature and interstitium of a representative mouse from each group.
Figure 12B:
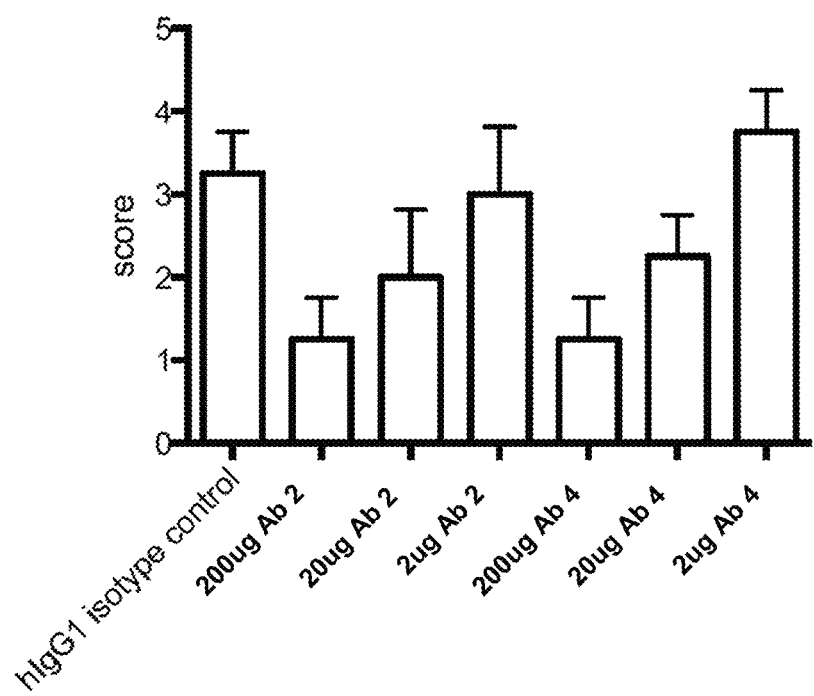
FIG. 12B is a bar graph showing the histological scoring of the mouse lungs shown in FIG. 12A. The scores were the average scores of all mice in each experimental group and time point.

Histological analysis was also performed at 4 days post-infection on lungs from mice treated at 24 hours pre-infection with Ab 2, Ab 4, or hIgG1 isotype control antibody (FIG. 12A). For example, the degrees of interstitial, peri-bronchiolar, and perivascular inflammation were scored from 0 to 5. Other histologic features, such as the presence of bronchiolar epithelial and alveolar damage, pleural changes and the extent of peribronchovascular inflammation, were also analyzed. An overall inflammatory score for each mouse was averaged for each experimental group, and the scores were presented as average scores of all mice in each group and time point (FIG. 12B).

Lungs from mice pre-treated with hIgG1 isotype control mice displayed significant lung pathology with increased interstitial inflammation, perivascular cuffing, and thickening of alveolar septa. Mice treated with 200 μg of either Ab 2 or Ab 4 had reduced inflammation with minimal foci of inflammatory cells in the interstitium, minor bronchiolar cuffing, and less alveolar wall thickening. In mice pre-treated with 20 μg of Ab 2 and Ab 4, there were moderate levels of perivascular cuffing and interstitial inflammation compared to the higher dose antibody group. The 2 μg antibody pre-treated group had similar pathology to the hIgG1 isotype control, displaying significant interstitial inflammation and predominant peri-vascular inflammation. Blinded histological scoring demonstrated reduced inflammation scores for treated mice (FIG. 12B). These findings demonstrate that anti-MERS-CoV antibodies, such as Ab 2 and Ab 4, confer a dose-dependent reduction in lung pathology following MERS-CoV infection, corroborating viral RNA levels and virus titers in the mice.

Thus, anti-MERS-CoV antibodies, such as Ab 2 and Ab 4, were effective in an in vivo model of MERS-CoV infection—the antibodies blocked MERS-CoV infection and disease in vivo when injected before infection, e.g., 1 day before infection.

Example 6

Antibody Treatment of Humanized DPP4 Mice that have been Infected with MERS-CoV

Figure 13A:
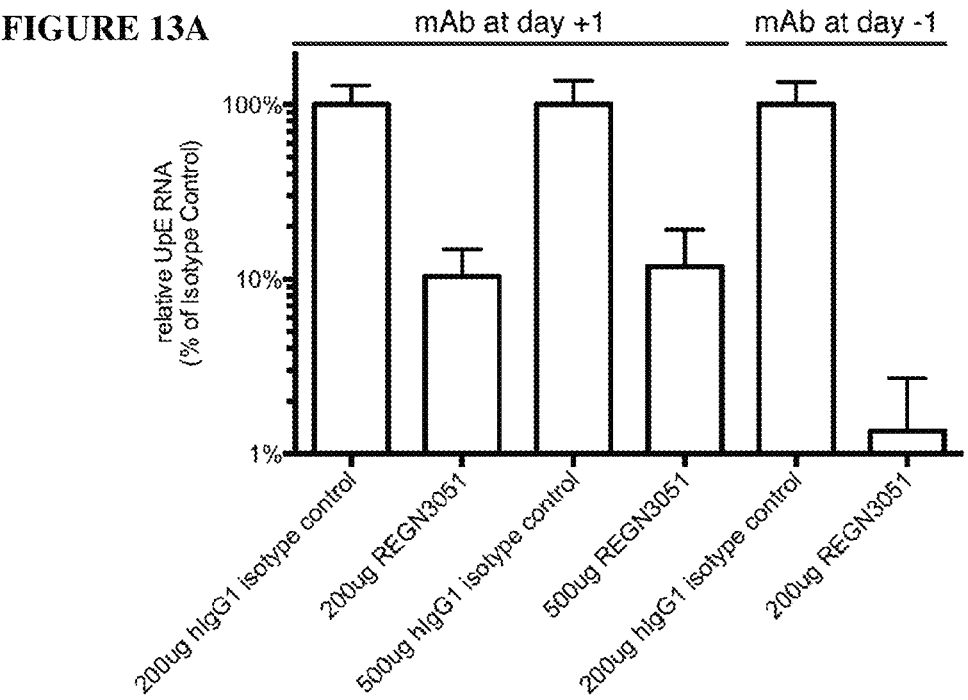
FIG. 13A is a bar graph showing quantitative PCR measurements of MERS-CoV genome (UpE RNA) from infected lungs. Effects of anti-MERS-CoV spike protein antibodies (Ab 2 or Ab 4) injected one day before or one day after viral infection were compared.
Figure 13B:
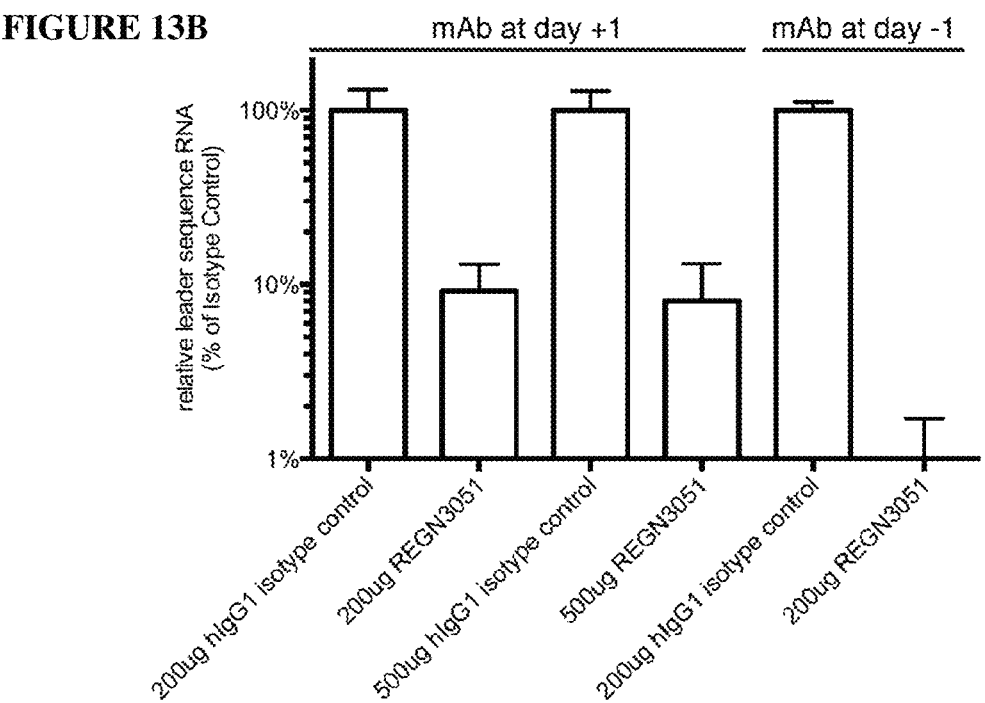
FIG. 13B is a bar graph showing quantitative PCR measurements of MERS-CoV mRNA transcript (leader RNA) from infected lungs. Effects of anti-MERS-CoV spike protein antibodies (Ab 2 or Ab 4) injected one day before or one day after viral infection were compared. For FIG. 13A and FIG. 13B, RNA was quantified using primers directed against the MERS-CoV genome and compared to hIgG1 isotype control treated mice. All samples were compared to hIgG1 control set at 100%.
Figure 13C:
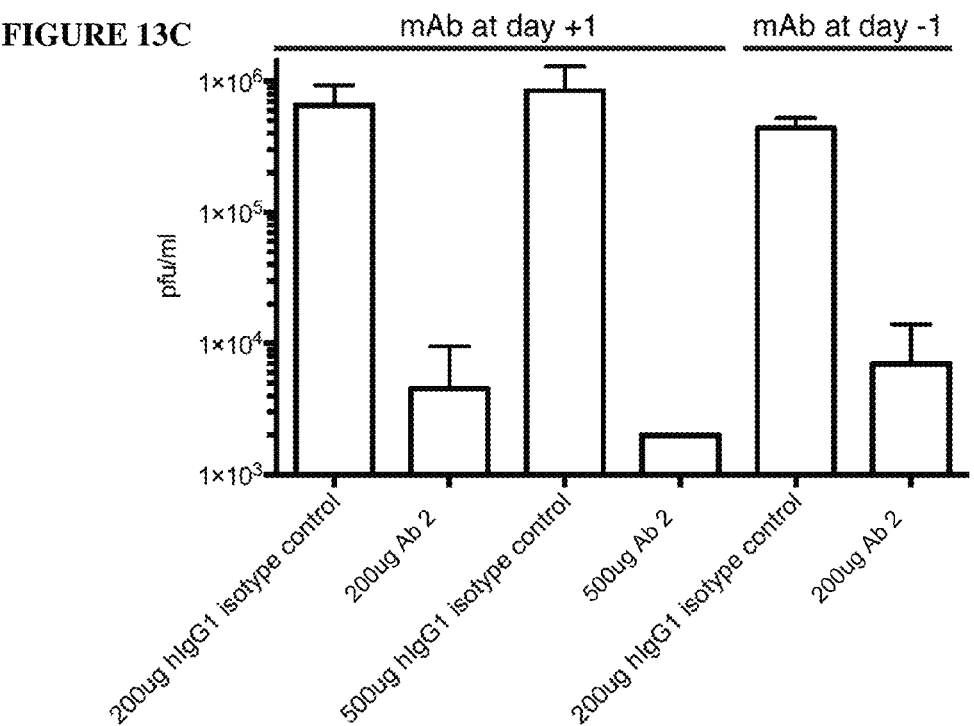
FIG. 13C is a bar graph showing the viral titer in lungs of mice treated with anti-MERS-CoV spike protein antibodies (Ab 2 or Ab 4) after viral infection. Viral titer was quantitated by plaque assay and reported as PFU/mL lung. Effects of antibodies injected one day before or one day after viral infection were compared.

To determine the therapeutic effect (e.g., ability to inhibit MERS-CoV replication and lung pathology after infection) of anti-MERS-CoV antibodies (e.g., Ab 2 or Ab 4), humanized DPP4 mice were infected with MERS-CoV. At 24 hours post-infection, the mice were injected i.p. with either 500 µg of hIgG1 isotype control or Ab 2 at 500 µg or 200 µg. At 4 days post-infection, mice were euthanized and mouse lungs analyzed for viral RNA, virus titer, and lung pathology. Both the 500 µg and 200 µg doses of Ab 2 reduced viral RNA levels by about 10 fold in the lungs of mice compared to control antibody treated mice (FIGS. 13A-B). Lung titers of the same mice demonstrated significant reduction in viral levels in the lungs, with a greater than 2 log reduction at day 4 post-infection (FIG. 13C). These data demonstrate that after infection, e.g., 24 hours post-infection, an anti-MERS-CoV antibody (e.g., Ab 2) significantly inhibited viral replication.

Figure 14A:
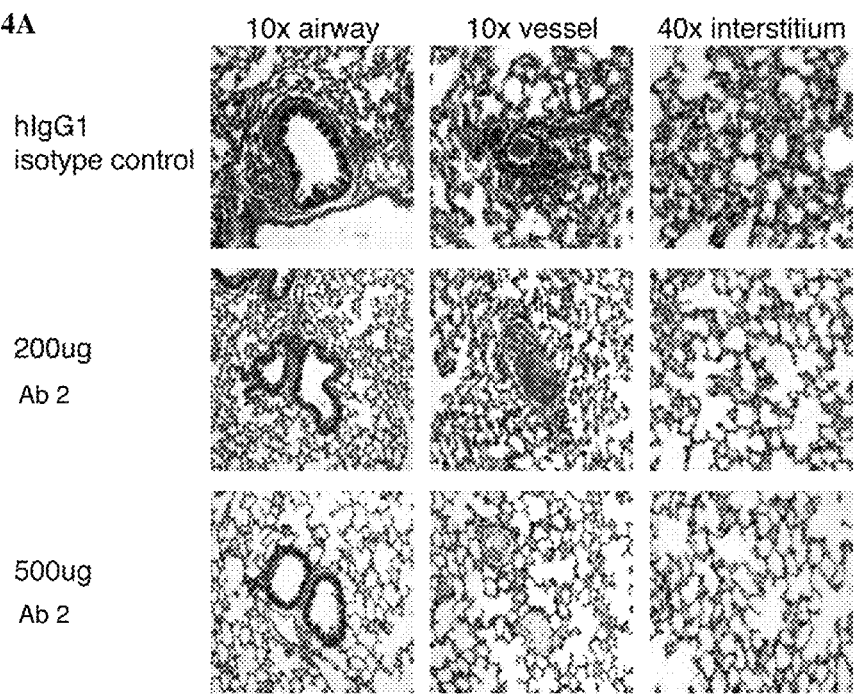
FIG. 14A is a panel of histological images of lungs from MERS-CoV infected B6/hDPP4 mice with anti-MERS-CoV spike protein Ab 2 antibody treatment at 1 day post-infection. Hematoxylin and Eosin stained sections of mouse lung show airway, vasculature, and interstitium of a representative mouse from each group.
Figure 14B:
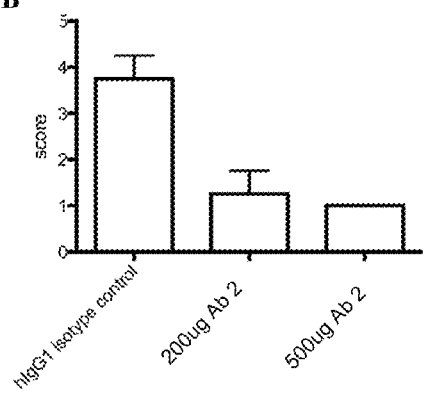
FIG. 14B is a bar graph showing the histological scoring of the mouse lungs of FIG. 14A.
Figure 15:
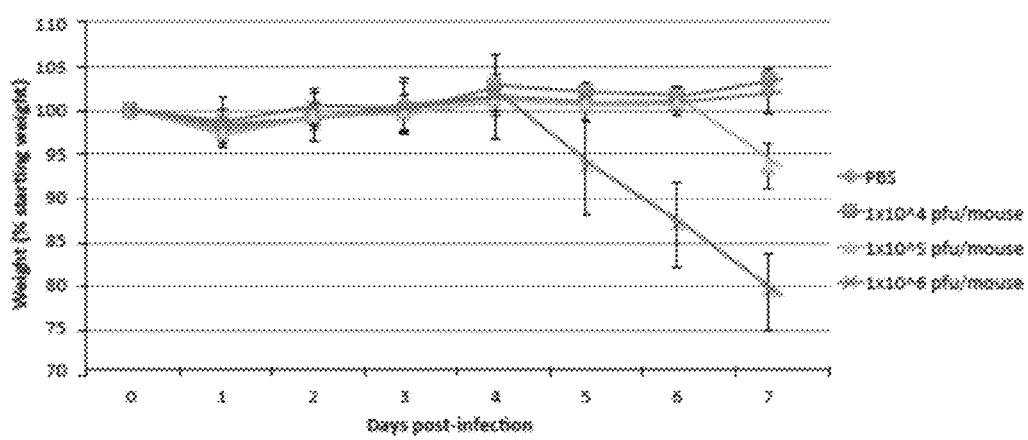
FIG. 15 depicts a dose-response study of weight as a function of time post-infection with MERS-CoV in humanized DPP4 mice. 4-5 mice are used per group.

Histological analysis was also performed on mice treated 24 hours post-infection with hIgG1 control antibody, 500 µg Ab 2, or 200 µg Ab 2 (FIGS. 14A-B). Mice treated with control antibody displayed similar pathology to the controls in Examples 2 and 5, with significant interstitial inflammation, peri-vascular cuffing, and thickening of alveolar septa. Mice treated with either 200 µg or 500 µg of Ab 2 had minimal interstitial inflammation with reduced and only focal peri-vascular inflammation throughout the lungs. Blinded histological scoring demonstrated reduced inflammation scores for treated mice (FIG. 14B). The data demonstrate that therapeutic doses of anti-MERS-CoV antibodies (e.g., Ab 2) reduced MERS-CoV induced lung pathology even when given after infection, e.g., 24 hours post-infection.

The invention claimed is:

1. A rodent, comprising a humanization of an endogenous rodent Dpp4 gene, wherein the humanization comprises a replacement at the endogenous rodent Dpp4 locus of a rodent gene encoding an exon of an Dpp4 gene with a nucleic acid sequence encoding at least one exon of a human DPP4 gene to form a modified DPP4 gene, wherein expression of the modified DPP4 gene is under control of rodent regulatory elements at the endogenous rodent Dpp4 locus, wherein the rodent is a mouse or a rat, and wherein the rodent exhibits one or more symptoms when infected with Middle East respiratory syndrome coronavirus (MERS-CoV).

2. The rodent of claim 1, wherein the human DPP4 gene encoding a human or humanized DPP4 protein comprises exon 2 through exon 26 of the human DPP4 gene.

3. The rodent of claim 2, wherein the humanized DPP4 protein comprises the extracellular domain of the human DPP4 protein.

4. The rodent of claim 3, wherein the humanized DPP4 protein comprises the transmembrane domain and cytoplasmic domain of the mouse Dpp4 protein.

5. The rodent of claim 1, wherein the rodent is a mouse that is incapable of expressing a mouse Dpp4 protein.

6. The rodent of claim 1, wherein the humanization of the endogenous rodent Dpp4 gene is heterozygous.

7. The rodent of claim 1, wherein the humanization of the endogenous rodent Dpp4 gene is homozygous.

8. A method for making a humanized rodent, comprising replacing a rodent Dpp4 gene sequence encoding rodent Dpp4 protein with a human DPP4 gene sequence comprising one or more exons of the human DPP4 gene sequence encoding human or humanized DPP4 protein, wherein the replacement is at an endogenous rodent Dpp4 locus and the human DPP4 gene sequence comprising one or more exons of the human DPP4 gene sequence encoding human or humanized DPP4 protein is operably linked to rodent regulatory elements or sequences at the endogenous rodent Dpp4 locus, wherein the rodent is a mouse or a rat, and wherein the rodent exhibits one or more symptoms when infected with Middle East respiratory syndrome coronavirus (MERS-CoV).

9. The method of claim 8, wherein the rodent regulatory elements or sequences are from a mouse or a rat.

10. The method of claim 8, wherein the rodent regulatory elements or sequences are endogenous rodent regulatory elements or sequences at the rodent Dpp4 locus.

11. The method of claim 8, wherein the human DPP4 gene sequence replacing the rodent Dpp4 gene sequence comprises at least one exon of the human DPP4 gene sequence.

12. The method of claim 11, wherein the human DPP4 gene sequence replacing the rodent Dpp4 gene sequence comprises at least 2, 3, 4, 5, 6, 7, 8, 9, 10, 11, 12, 13, 14, 15, 16, 17, 18, 18, 20, 21, 22, 23, 24, or 25 exons of the human DPP4 gene sequence.

13. The method of claim 11, wherein the human DPP4 gene sequence replacing the rodent Dpp4 gene sequence comprises all 26 exons of the human DPP4 gene sequence.

14. The method of claim 8, wherein the human DPP4 gene sequence replacing the rodent Dpp4 gene sequence comprises at least one exon of the human DPP4 gene sequence encoding the extracellular domain of the human DPP4 protein.

15. The method of claim 14, wherein the human DPP4 gene sequence replacing the rodent Dpp4 gene sequence comprises at least 2, 3, 4, 5, 6, 7, 8, 9, 10, 11, 12, 13, 14, 15, 16, 17, 18, 18, 20, 21, 22, or 23 exons of the human DPP4 gene sequence encoding the extracellular domain of the human DPP4 protein.

16. The method of claim 14, wherein the human DPP4 gene sequence replacing the rodent Dpp4 gene sequence comprises all 24 exons of the human DPP4 gene sequence encoding the extracellular domain of the human DPP4 protein.

17. The method of claim 8, wherein the rodent is heterozygous for the human DPP4 gene sequence comprising one or more exons of the human DPP4 gene sequence encoding the human or humanized DPP4 protein.

18. The method of claim 8, wherein the rodent is homozygous for the human DPP4 gene sequence comprising one or more exons of the human DPP4 gene sequence encoding the human or humanized DPP4 protein.

19. A method for determining the in vivo therapeutic efficacy of a human-specific DPP4 antagonist in the rodent of claim 1, the method comprising:
 (a) administering to the rodent a DPP4 antagonist, wherein the rodent is infected with Middle East respiratory syndrome coronavirus (MERS-CoV); and
 (b) determining if the DPP4 antagonist treats or prevents one or more symptoms of MERS-CoV infection compared to control rodents infected with MERS-CoV who have not been administered the DPP4 antagonist.

20. The method of claim 19, wherein the DPP4 antagonist is selected from the group consisting of small molecules, peptides and antibodies.

21. The method of claim 19, wherein the DPP4 antagonist is an antibody to a MERS-CoV protein.

22. The method of claim 21, wherein the MERS-CoV protein is MERS-CoV spike protein.

23. The method of claim 19, wherein the antagonist is administered before MERS-CoV infection.

24. The method of claim 19, wherein the antagonist is administered after MERS-CoV infection.

25. The method of claim 19, wherein the antagonist is administered simultaneously with MERS-CoV infection.

26. The method of claim 19, wherein the symptom of MERS-CoV infection is viral titer or RNA level.

27. The method of claim 26, wherein viral titer or RNA level is assessed by one or more methods selected from the group consisting of qPCR, Northern Blot, plaque assay, and in situ hybridization.

28. The method of claim 19, wherein the symptom of MERS-CoV infection is lung inflammation.

29. The method of claim 28, wherein lung inflammation is assessed histochemically.

30. The method of claim 19, wherein the symptom of MERS-CoV infection is weight loss.

* * * * *